(12) United States Patent
Bobka et al.

(10) Patent No.: US 9,334,226 B2
(45) Date of Patent: May 10, 2016

(54) COPPER-PROMOTED SHELL CATALYST FOR PRODUCING ALKENYL CARBOXYLIC ACID ESTERS

(71) Applicant: Clariant International Ltd., Muttenz (CH)

(72) Inventors: Roman Bobka, Munich (DE); Gerhard Mestl, Munich (DE); Peter Scheck, Gilching (DE); Carolin Fischer, Rosenheim (DE); Martin Schoenfelder, Tuntenhausen (DE)

(73) Assignee: Clariant International Ltd., Muttenz (CH)

( * ) Notice: Subject to any disclaimer, the term of this patent is extended or adjusted under 35 U.S.C. 154(b) by 58 days.

(21) Appl. No.: 14/031,587

(22) Filed: Sep. 19, 2013

(65) Prior Publication Data
US 2014/0081041 A1 Mar. 20, 2014

(30) Foreign Application Priority Data

Sep. 19, 2012 (DE) .................. 10 2012 018 448
Apr. 23, 2013 (DE) .................. 10 2013 006 945

(51) Int. Cl.
| | |
|---|---|
| *C07C 67/055* | (2006.01) |
| *B01J 23/66* | (2006.01) |
| *B01J 23/58* | (2006.01) |
| *B01J 23/89* | (2006.01) |
| *B01J 37/02* | (2006.01) |
| *B01J 23/62* | (2006.01) |
| *B01J 35/00* | (2006.01) |
| *B01J 35/10* | (2006.01) |
| *B01J 37/18* | (2006.01) |

(52) U.S. Cl.
CPC ............. *C07C 67/055* (2013.01); *B01J 23/626* (2013.01); *B01J 23/66* (2013.01); *B01J 23/8926* (2013.01); *B01J 23/8946* (2013.01); *B01J 35/002* (2013.01); *B01J 35/008* (2013.01); *B01J 35/108* (2013.01); *B01J 37/0242* (2013.01); *B01J 37/0244* (2013.01); *B01J 37/18* (2013.01)

(58) Field of Classification Search
CPC ...... C07C 67/055; B01J 23/8946; B01J 23/66
See application file for complete search history.

(56) References Cited

U.S. PATENT DOCUMENTS

| | | | |
|---|---|---|---|
| 4,048,096 A | 9/1977 | Bissot | |
| 5,066,365 A | 11/1991 | Roscher et al. | |
| 5,347,046 A * | 9/1994 | White et al. | .............. 560/245 |
| 6,015,769 A | 1/2000 | Wang | |

FOREIGN PATENT DOCUMENTS

| | | |
|---|---|---|
| EP | 0654301 | 5/1995 |
| GB | 1188777 | 4/1970 |
| WO | WO 9637294 | 11/1996 |
| WO | WO 9818553 | 5/1998 |
| WO | WO 99/62632 A1 | 12/1999 |

OTHER PUBLICATIONS

Gawande et al, Catalysis Science &Technology, Role of mixed metal oxides in catalysis science-versatile applications in organic synthesis, 2012, 2, pp. 1113-1125.*
PCT International Search Report for PCT/US99/10992, mailed Aug. 20, 1999.

* cited by examiner

*Primary Examiner* — Paul A Zucker
(74) *Attorney, Agent, or Firm* — Anthony A. Bisulca

(57) ABSTRACT

A method for producing a shell catalyst which is suitable for the synthesis of alkenyl carboxylic acid esters, in particular for producing vinyl acetate monomer (VAM) from ethylene or allyl acetate monomer from propylene by means of oxy-acetylation. Also, a shell catalyst that can be obtained by the method according to the invention, as well as the use of the shell catalyst produced using the method for producing alkenyl carboxylic acid esters, in particular vinyl acetate monomer (VAM) and allyl acetate monomer.

15 Claims, 8 Drawing Sheets

COPPER-PROMOTED SHELL CATALYST FOR PRODUCING ALKENYL CARBOXYLIC ACID ESTERS

FIELD

The present invention relates to a method for producing a shell catalyst which is suitable for the synthesis of alkenyl carboxylic acid esters, in particular for producing vinyl acetate monomer (VAM) from ethylene or allyl acetate monomer from propylene by means of oxy-acetylation. The present invention also relates to a shell catalyst that can be obtained by the method according to the invention as well as the use of the shell catalyst produced using the method according to the invention or of the shell catalyst according to the invention for producing alkenyl carboxylic acid esters, in particular vinyl acetate monomer (VAM) and allyl acetate monomer.

BACKGROUND

Supported catalysts which contain palladium and gold and optionally additional further metal promoters have already been known for some time. Vinyl acetate monomer is usually produced in the presence of catalysts containing palladium and gold from a reaction mixture of ethylene, oxygen and acetic acid. Various production methods for such supported catalysts are already known. Thus, for example, precursor compounds which contain the corresponding metals are applied, dissolved preferably in an aqueous solution, to the surface of a support body. The support body containing the corresponding precursor compounds is then usually calcined under oxidizing conditions in a high-temperature oven, wherein the metal-containing precursor compounds are converted to the metal oxides. The support bodies which contain the corresponding metal oxides are then subjected to reduction to the elemental metals. In some known methods, however, precursor compounds are used in which an oxidation to the metal oxides is not necessary and the reduction step can be carried out gently directly after the drying.

VAM is an important component for the production of polyvinyl acetate, vinyl acetate copolymers (such as ethylene vinyl acetates or ethylene vinyl alcohol copolymers) and polyvinyl alcohol. Because of the wide field of use of these polymers, for example as binders in the construction, paints, and varnishes sectors and as raw material for the adhesive, paper and textile industries, there is still a high demand for VAM and for constant improvement of the activity and selectivity of catalysts for its production.

Normally, in the synthesis of VAM, shell catalysts are used in which at least elemental palladium and gold are situated in an outer shell of the catalyst support body (hereafter called support body or shaped body). In addition, however, these shell catalysts can also contain further metals as promoters. To produce them, a mixed solution of a Pd-containing precursor compound and an Au-containing precursor compound is normally applied to a catalyst support body which is then dried, and the metal components of the precursor compounds are converted to the elemental metals. The Pd/Au combination normally leads to a good selectivity or activity of the catalyst. In addition, due to the capital intensity of VAM production plants and increasingly high raw material costs, in particular for ethylene, there is a constant requirement to optimize the economic efficiency of the method for producing VAM by means of improved catalysts. In the production of VAM shell catalysts which contain further metal promoters in addition to Pd and Au, an additional preparation step for the addition of promoters is usually added, which makes the production method for such catalysts very expensive in terms of preparation.

SUMMARY

The object of the present invention was therefore to provide a method for producing a shell catalyst which results in a shell catalyst that outperforms previous catalysts in respect of the activity and selectivity in the synthesis of alkenyl carboxylic acid esters. Another object of the present invention was to provide a method for producing a promoted shell catalyst in which no additional step of applying a promoter compound is necessary, with the result that the method can be simplified in terms of preparation.

Furthermore, all the conventional methods for producing VAM catalysts have proved to be capable of improvement in respect of their noble metal yield. The noble metal yield here is calculated from the quantity of noble metal, thus Pd and Au and optionally a further promoter metal, that remains on the catalyst in the end after all production steps, and from the noble metal quantity to be used for this in the production. It was therefore also an object of the present invention to improve the noble metal yield in the production of the corresponding catalysts.

These objects have been achieved by a method according to the invention with which shell catalysts with significantly increased selectivity and activity can be produced.

The method according to the invention for producing a shell catalyst comprises the following steps:
  a) applying an acetate compound to a support body; and
  b) sequentially or simultaneously applying a Pd precursor compound and an Au precursor compound to the support body obtained after step (a);
characterized in that in one of steps (a) and (b) a Cu and/or Sn precursor compound is additionally applied to the support body.

DETAILED DESCRIPTION

The abbreviation "VAM" is used below in this application not only for vinyl acetate monomer, but generally for alkenyl carboxylic acid ester.

By the term "shell catalyst" is meant a catalyst which comprises a support body and a shell with catalytically active material, wherein the shell can be formed in two different ways: Firstly, a catalytically active material can be present in the outer area of the support body, with the result that the material of the support body serves as matrix for the catalytically active material and the area of the support body which is impregnated with the catalytically active material forms a shell around the unimpregnated core of the support body. Secondly, an additional layer in which a catalytically active material is present can be applied to the surface of the support body. This layer thus forms an additional material layer which is constructed as a shell around the support body. In the latter variant, the support body material is not a constituent of the shell, but the shell is formed by the catalytically active material itself or a matrix material which comprises a catalytically active material.

In the shell catalyst produced by the method according to the invention, the metals are present either in monoatomic form or in the form of aggregates. However, they are preferably present in the form of aggregates. The monoatomic atoms or multiatomic aggregates are dispersed predominantly uniformly inside the shell of the shell catalyst. By a multiatomic aggregate is meant the clustering of several metal atoms to form a composite which lies between monoatomic form and metallic type (alloy). The term also includes so-called metal clusters.

The shell thickness of the outer shell of the support body is preferably 1 to 50%, more preferably 2 to 40%, even more preferably 3 to 30% and most preferably 4 to 20% of half of the total thickness of the support body. The named percentage therefore relates to half of the total thickness as, depending on the shape of the support body during production, e.g. by spray impregnation with a solution containing precursor compound, the precursor compound either penetrates the support body material from two outer surfaces (sphere) or, if the support body material has a more complex shape, such as e.g. that of a hollow cylinder, it has an outer surface and an inner surface which the precursor compound penetrates. In the case of support body materials deviating from sphere geometry the total thickness of the support body is measured along the longest support body axis. The outer shell boundary is equalized with the outer boundary of the metal-containing support body. By inner shell boundary is meant the boundary, located inside the support body, of the metal-containing shell which is at such a distance from the outer shell boundary that 95 wt.-% of all of the metal contained in the support body is located in the outer shell. However, the shell thickness is preferably not more than 50%, more preferably not more than 40%, even more preferably not more than 30% and most preferably not more than 20%, in each case relative to half of the total thickness of the support body.

The metal-impregnated support body preferably contains no more than 5% of the total metal in its inner area, thus inside the area that is delimited to the outside by the inner shell boundary of the metal shell.

The support body preferably consists of an inert material. It can be porous or non-porous. However, the support body is preferably porous. The support body preferably consists of particles with a regular or irregular shape, such as for example spheres, tablets, cylinders, solid cylinders or hollow cylinders, rings, stars or other shapes, and its dimensions, such as e.g. diameter, length or width, are in a range of from 1 to 10 mm, preferably 3 to 9 mm. Spherical, i.e. e.g. sphere-shaped, particles with a diameter of from 3 to 8 mm are preferred according to the invention. The support body material can be composed of any non-porous or porous substance, preferably porous substance. Examples of materials for this are titanium oxide, silicon oxide, aluminium oxide, zirconium oxide, magnesium oxide, silicon carbide, magnesium silicate, zinc oxide, zeolites, sheet silicates and nanomaterials, such as for example carbon nanotubes or carbon nanofibres.

The above-named oxidic support body materials can be used for example in the form of mixed oxides or defined compositions, such as for example $TiO_2$, $SiO_2$, $Al_2O_3$, $ZrO_2$, MgO, SiC or ZnO. Furthermore, soots, ethylene black, charcoal, graphite, hydrotalcites or further support body materials known per se to a person skilled in the art can preferably be used in different possible modifications. The support body materials can preferably be doped for instance with alkali or alkaline earth metals or also with phosphorus, halide and/or sulphate salts. The support body preferably comprises an Si—Al mixed oxide, or the support body consists of an Si—Al mixed oxide. The support body, preferably an Si—Al mixed oxide, can in addition also be doped with Zr and preferably contains this in a proportion of from 5 to 30 wt.-%, relative to the total weight of the support body.

The BET surface area of the support body material without the coating with the precursor compounds is 1 to 1,000 $m^2/g$, preferably 10 to 600 $m^2/g$, particularly preferably 20 to 400 $m^2/g$ and quite particularly preferably between 80 and 170 $m^2/g$. The BET surface area is determined using the 1-point method by adsorption of nitrogen in accordance with DIN 66132.

In addition, it can be preferred that the integral pore volume of the support body material (determined in accordance with DIN 66133 (Hg porosimetry)) without the coating with the precursor compound is >0.1 ml/g, preferably >0.18 ml/g.

The support body is usually produced by subjecting a plurality of support bodies to a "batch" process, in the individual method steps of which the shaped bodies are subject to relatively high mechanical stresses for example by using stirring and mixing tools. In addition, the shell catalyst produced by the method according to the invention can be subjected to a strong mechanical load stress during the filling of a reactor, which can result in an undesired formation of dust as well as damage to the support body, in particular to its catalytically active shell located in an outer area.

In particular, to keep the abrasion of the catalyst produced by the method according to the invention within reasonable limits, the shell catalyst has a hardness of ≥20 N, preferably of ≥25 N, further preferably of ≥35 N and most preferably of ≥40 N. The hardness is ascertained by means of an 8M tablet-hardness testing machine from Dr. Schleuniger Pharmatron AG, determining the average for 99 shell catalysts, after drying of the catalyst at 130° C. for 2 hours, wherein the apparatus settings are as follows:
Distance from the shaped body: 5.00 mm
Time delay: 0.80 s
Feed type: 6 B
Speed: 0.60 mm/s The hardness of the shell catalyst produced by the method according to the invention can be influenced for example by means of variation in certain parameters of the method for producing the support body, for example by the calcining time and/or the calcining temperature of the support body. The just-mentioned calcining is not a calcining of the support body impregnated with the metal-containing precursor compounds, but merely a calcining step for producing the support body before the precursor compounds are applied.

It is also preferred that at least 80% of the integral pore volume of the support body is formed by mesopores and macropores, preferably at least 85% and most preferably at least 90%. This counteracts a reduced activity, effected by diffusion limitation, of the catalyst produced by the method according to the invention, in particular in the case of metal-containing shells with relatively large thicknesses. By the terms micropores, mesopores and macropores are meant in this case pores which have a diameter of <2 nm, a diameter of from 2 to 50 nm and a diameter of >50 nm respectively.

The activity of the shell catalysts produced by the method according to the invention normally depends on the quantity of the metal loading in the shell: As a rule, the more metal there is in the shell, the higher the activity. The thickness of the shell here has a smaller influence on the activity, but is a decisive variable with respect to the selectivity of the catalysts. With equal metal loading of the catalyst support, the smaller the thickness of the outer shell of the catalyst is, the higher the selectivity of the shell catalysts produced by the method according to the invention is in general. It is thus decisive to set an optimum ratio of metal loading to shell thickness in order to guarantee the highest possible selectivity with the highest possible activity. It is therefore preferred that the shell of the shell catalyst produced according to the invention has a thickness in the range of from 20 μm to 1,000 μm, more preferably from 30 μm to 800 μm, even more preferably from 50 μm to 500 μm and most preferably from 100 μm to 300 μm.

The thickness of the shell can be measured visually by means of a microscope. The area in which the metal is deposited appears black after its reduction in hydrogen, while the areas free of noble metals appear white. As a rule, in the case of shell catalysts produced according to the invention the boundary between areas containing noble metals and areas free of them is very sharp and can be clearly recognized visually. If the above-named boundary is not sharply defined and accordingly not clearly recognizable visually, the thickness of the shell corresponds—as already mentioned—to the thickness of a shell, measured starting from the outer surface of the catalyst support, which contains 95% of the noble metal deposited on the support. In order to ensure a largely uniform activity of the catalyst produced by the method according to the invention over the thickness of the noble metal-containing shell, the noble metal concentration should vary only relatively little over the shell thickness. It is therefore preferred that, over an area of 90% of the shell thickness, wherein the area is at a distance of 50% of the shell thickness from each of the outer and inner shell limits, the profile of the noble metal concentration of the catalyst varies from the average noble metal concentration of this area by a maximum of +/−20%, preferably by a maximum of +/−15% and by preference by a maximum of +/−10%. Such profiles can be achieved for example by means of physical deposition methods, such as spray impregnation of a solution containing the precursor compound onto support bodies circulated in a gas. The support bodies here are preferably located in a so-called fluidized bed or in a fluid bed, but all devices in which the support bodies can be swirled in a gas glide layer are also conceivable. The named shell profiles can particularly preferably be obtained by means of the spraying-on described further below in a fluidized bed, a fluid bed or an Innojet AirCoater. In the case of the shell catalysts produced according to the invention, the named distribution of the metal loading preferably describes a rectangular function, i.e. the concentration does not decrease or only decreases imperceptibly over the course of the inside of the support body and ends with a relatively "sharp" boundary (see above-named distribution parameters). In addition to the rectangular function, the metal loading inside the shell can however also describe a triangular or trapezium function in the case of which the metal concentration gradually decreases from the outside to the inside in the shell. However, a metal distribution according to the rectangular function is particularly preferred.

Contrary to the views held until now with respect to the production of VAM, however, a metal distribution according to the rectangular function is particularly preferred.

Contrary to the views held until now with respect to the production of vinyl acetate monomer catalysts, the applicants of the present application have surprisingly discovered that the application of an acetate, for example in the form of an alkali acetate, to a support body before the application of the metal precursor compounds and before the reduction of the metal components of the precursor compounds leads to a VAM shell catalyst which has a much higher activity and selectivity than shell catalysts in which the acetate is applied after the application of the metal precursor compounds and/or after the reduction of the metal components of the precursor compounds.

The acetate (acetate compound) to be used in step a) of the method according to the invention is preferably an alkali or alkaline earth acetate, in particular an alkali acetate. The alkali acetate can be lithium acetate, sodium acetate, potassium acetate, caesium acetate or rubidium acetate, but preferably potassium acetate.

The Pd precursor compounds and Au precursor compounds used in the method according to the invention are preferably water-soluble compounds.

The Pd precursor compound used in the method according to the invention is preferably selected from: nitrate compounds, nitrite compounds, acetate compounds, tetraamine compounds, diamine compounds, hydrogen carbonate compounds and hydroxidic metallate compounds.

Examples of preferred Pd precursor compounds are water-soluble Pd salts. The Pd precursor compound is particularly preferably selected from the group consisting of $Pd(NH_3)_4(HCO_3)_2$, $Pd(NH_3)_4(HPO_4)$, ammonium Pd oxalate, Pd oxalate, $K_2Pd(oxalate)_2$, Pd(II) trifluoroacetate, $Pd(NH_3)_4(OH)_2$, $Pd(NO_3)_2$, $H_2Pd(OAc)_2(OH)_2$, $Pd(NH_3)_2(NO_2)_2$, $Pd(NH_3)_4(NO_3)_2$, $H_2Pd(NO_2)_4$, $Na_2Pd(NO_2)_4$, $Pd(OAc)_2$ as well as freshly precipitated $Pd(OH)_2$.

If freshly precipitated $Pd(OH)_2$ is used, it is preferably produced as follows: A 0.1 to 40 wt.-% aqueous solution is preferably produced from tetrachloropalladate. A base is then preferably added to this solution, until a brown solid, namely $Pd(OH)_2$, precipitates. To produce a solution for application to the catalyst support, the freshly precipitated $Pd(OH)_2$ is isolated, washed and dissolved in an aqueous alkaline solution.

The compound $Pd(NH_3)_4(OH)_2$ is preferably produced as follows: A precursor compound such as e.g. $Na_2PdCl_4$ is—as previously described—precipitated with potassium hydroxide solution to palladium hydroxide, and the precipitate, after filtration and washing, is dissolved in aqueous ammonia to form $Pd(NH_3)_4(OH)_2$.

Furthermore, the Pd nitrite compounds can also be used in the method according to the invention. Preferred Pd nitrite precursor compounds are for example those which are obtained by dissolving $Pd(OAc)_2$ in an $NaNO_2$ or $KNO_2$ solution.

However, the above-named hydroxo complexes or hydroxo compounds are particularly preferably used as Pd precursor compounds. The compound $Pd(NH_3)_4(OH)_2$ is quite particularly preferably used as Pd precursor compound.

The Au precursor compounds used in the method according to the invention are preferably selected from: acetate compounds, nitrite or nitrate compounds and oxidic or hydroxidic metallate compounds.

Examples of preferred Au precursor compounds are water-soluble Au salts. The Au precursor compound is preferably selected from the group consisting of $KAuO_2$, $NaAuO_2$, $LiAuO_2$, $RbAuO_2$, $CsAuO_2$, $Ba(AuO_2)_2$, $NaAu(OAc)_3(OH)$, $KAu(NO_2)_4$, $KAu(OAc)_3(OH)$, $LiAu(OAc)_3(OH)$, $RbAu(OAc)_3(OH)$, $CsAu(OAc)_3(OH)$, $HAu(NO_3)_4$ and $Au(OAc)_3$. It may be advisable to add the $Au(OAc)_3$ or one of the named aurates in each case freshly by precipitation as oxide or hydroxide from an auric acid, washing and isolating the precipitate as well as taking up same in acetic acid or alkali hydroxide respectively. One of the named alkali aurates is particularly preferably used as Au-containing precursor compound, which is used in dissolved form for application to the support. The production of a potassium aurate solution is known in the literature and can be carried out in accordance with the production methods disclosed in the documents WO99/62632 and U.S. Pat. No. 6,015,769. The other alkali aurates can also be produced in the same way. It is particularly preferred that $KAuO_2$ or $CsAuO_2$ or their hydroxides dissolved in water ($KAu(OH)_4$) and ($CsAu(OH)_4$) are used as Au precursor compound in the method according to the invention.

The Cu precursor compound is preferably a water-soluble compound. The copper compound can be copper chloride (anhydrous or as dihydrate) or a water-soluble chloride-free copper precursor compound. It is particularly preferred that the Cu precursor compound is a chloride-free precursor compound. The chloride-free Cu precursor compound is preferably selected from one of the following compounds: copper acetate (anhydrous or as monohydrate), copper nitrate (as trihydrate or hexahydrate), copper sulphate (anhydrous or as pentahydrate), copper formate (anhydrous or as pentahydrate) and the like.

The Sn precursor compound is preferably a water-soluble compound. The tin compound can be tin chloride (anhydrous, as dihydrate or as pentahydrate) or a water-soluble chloride-free tin precursor compound. It is particularly preferred that the Sn precursor compound is a chloride-free precursor compound. The chloride-free Sn precursor compound is preferably selected from one of the following compounds: potassium stannate, metastannic acid, tin acetate and the like.

The named precursor compounds are mentioned herein only by way of example and any further precursor compounds can be used which are suitable for the production of a VAM shell catalyst. However, it is particularly preferred that the precursor compounds are substantially chloride-free. By substantially chloride-free is meant that the empirical formula of the compound comprises no chloride, but it is not ruled out that the compound contains unavoidable chloride impurities for example due to production conditions.

It is particularly preferred that $Pd(NH_3)_4(OH)_2$ is used as Pd precursor compound, potassium or caesium aurate as Au precursor compound, $Cu(OAc)_2$ as copper compound and $K_2SnO_3$ as tin compound.

To apply the acetate in step (a) of the method according to the invention, a solution containing the acetate is preferably produced. Water is preferably used, more preferably deionized water, as solvent for producing the solution. The concentration of the acetate in the solution preferably lies in the range of from 0.5 to 5 mol/L, more preferably 1 to 3 mol/L, even more preferably 1.5 to 2.5 mol/L and most preferably 1.9 to 2.1 mol/L.

The application of the solution containing the acetate can be carried out by any method known in the state of the art, such as for example wet-chemical impregnation, pore-filling method (incipient wetness) as well as by spray impregnation of any kind. Particularly preferably according to the invention, the acetate is applied to the support body by the pore-filling method or by spray impregnation of a solution containing the acetate.

During the application of the solution containing the acetate, the support can be present static, but is preferably moved. The movement of the support bodies can take place in any conceivable way, for example mechanically with a coating drum, mixing drum or also with the help of a support gas. If the application is carried out by spray impregnation, it is particularly preferred that the movement of the support bodies is carried out with the help of a support gas (or process gas), for example in a fluid bed, a fluidized bed or in a static coating chamber, for example an Innojet AirCoater, wherein hot air is preferably blown in, with the result that the solvent is quickly evaporated. The temperature here is preferably 15 to 80° C., more preferably 20 to 60° C. and most preferably 30 to 40° C. The spraying rate is preferably chosen during the spraying-on such that a balance is achieved between the evaporation rate of the solvent and the feed rate of the precursor compounds on the support body. It is particularly preferred that the spraying rate is constant during the spraying-in of the solution containing the acetate and lies in the range of a mass flow of from 0.1 g/min per 100 g to 10 g/min per 100 g of support body to be coated, more preferably in the range of from 0.25 to 7.5 g/min per 100 g and most preferably in the range of from 0.5 to 5 g/min per 100 g.

The solution containing acetate is preferably sprayed by a spraying nozzle into the apparatus, in which the fed-in spraying gas is preferably air.

The acetate anion loading preferably lies in the range of from 2.0 to 6.0 wt.-%, more preferably 2.5 to 5.5 wt.-% and most preferably 3.5 to 4.5 wt.-%, relative to the total weight of the support body dried after the application.

If the acetate is present as alkali acetate, the alkali metal loading lies in the corresponding stoichiometric ratio to the acetate anions.

After the application of the solution containing acetate, a drying is preferably carried out in the temperature range of from 20 to 180° C. in air, lean air or inert gas. The duration of the drying of the support bodies loaded with acetate preferably lies in the range of from 10 to 100 min, more preferably 30 to 60 min.

In step (b) of the method according to the invention the Pd precursor compound and the Au precursor compound are preferably present dissolved in solution. The Pd precursor compound and the Au precursor compound can be present dissolved in a mixed solution, but they can also each be dissolved in a separate solution. Pure solvents and solvent mixtures in which the selected metal compound(s) is/are soluble and which, after application to the catalyst support, can be easily removed again from same by means of drying are suitable as solvents for the transition metal precursor compounds. Preferred solvents are unsubstituted carboxylic acids, in particular acetic acid, ketones, such as acetone, and in particular water, in particular deionized water. The application of the precursor compounds in step (b) of the method according to the invention to the support body can be carried out by methods known per se. It is conceivable that the precursor compound(s) is/are applied by steeping, the pore-filling method (incipient wetness) or by spray impregnation of the solution(s) containing the precursor compound(s). In step (b) the precursor compounds can be applied either from a mixed solution containing the Au precursor compound and the Pd precursor compound or from two solutions each containing one of the two precursor compounds. The precursor compounds are particularly preferably applied to the support body in step (b) simultaneously from two different solutions. If the two precursor compounds are applied in step (b) from two different solutions, it is possible in principle that they are applied staggered, i.e. sequentially one after the other, or also in two time intervals which overlap.

The application of the precursor compounds in step (b) of the method according to the invention is preferably carried out by spraying the support body with a solution containing the precursor compound. Here too, it is preferred that the support bodies are moved in a process gas, e.g. in a coating drum, a fluid bed, a fluidized bed or in a static coating chamber of an Innojet AirCoater, wherein heated process gas is preferably blown in, with the result that the solvent is quickly evaporated. In this way, the precursor compounds are present in the named defined shell of the support body. The spraying rate is preferably chosen during the spraying-on such that a balance is achieved between the evaporation rate of the solvent and the feed rate of the precursor compounds on the support body. This makes it possible to set the desired shell thickness and palladium/gold distribution in the shell. Depending on the spraying rate, the shell thickness can thus be infinitely variably set and optimized, for example up to a thickness of 2 mm. But very thin shells with a thickness in the range of from 50 to 300 µm are thus also possible.

It is particularly preferred that the spraying rate in step (b) is constant and is in the range of a mass flow (the solution containing the precursor compound) of from 0.1 g/min per 100 g to 10 g/min per 100 g of support body to be coated, more preferably in the range of from 0.25 to 7.5 g/min per 100 g and most preferably in the range of from 0.5 to 5 g/min per 100 g. A mass flow above the given range leads to catalysts with lower activity; although a mass flow below the given range has no strongly negative effects on the catalyst performance, the catalyst production takes a very long time and the production is therefore inefficient.

If a fluid bed unit is used in step (a) and/or (b) of the method according to the invention, it is preferred if the support bodies circulate elliptically or toroidally in the fluid bed. To give an idea of how the support bodies move in such fluid beds, it may be stated that in the case of "elliptical circulation" the support bodies move in the fluid bed in a vertical plane on an elliptical path, the size of the main and secondary axes changing. In the case of "toroidal circulation" the support bodies move in the fluid bed in a vertical plane on an elliptical path, the size of the main and secondary axes changing, and in a horizontal plane on a circular path, the size of the radius changing. On average, the support bodies move in a vertical plane on an elliptical path in the case of an "elliptical circulation", on a toroidal path in the case of a "toroidal circulation", i.e. a support body travels helically over the surface of the torus with a vertically elliptical section.

It is particularly preferred in the method according to the invention in step (b) that the application of the precursor compounds to the catalyst support body impregnated with acetate, thus e.g. with alkali acetate, is carried out by means of a fluid bed in a fluid bed unit. It is particularly preferred that there is a so-called controlled glide layer of a process gas in the unit. For one thing, the support bodies are very thoroughly mixed by the controlled glide layer of a process gas, wherein they simultaneously rotate about their own axis, and are dried evenly by the process gas. For another, due to the consistent orbital movement, effected by the controlled glide layer of the process gas, of the support bodies the support bodies pass through the spray procedure (application of the precursor compounds) at a virtually constant frequency (also applies to step (a) of the method according to the invention). A largely uniform shell thickness, or penetration depth of the metals into the support body, of a treated batch of support bodies is thereby achieved. A further result is that the noble metal concentration varies only relatively slightly over a relatively large area of the shell thickness, whereby a largely uniform activity of the resulting catalyst is guaranteed over the thickness of the noble metal shell.

Furthermore, the support body used in the method according to the invention is preferably heated during a spray impregnation in step (b), for example by means of heated process gas. The process gas here preferably has a temperature of from 10 to 110° C., more preferably 40 to 100° C. and most preferably 50 to 90° C. The named lower limits should be adhered to in order to guarantee that the named outer shell has a small layer thickness with a high concentration of noble metal.

Air is preferably used as process gas in the spray impregnation in steps (a) and/or (b). However, inert gases such as e.g. nitrogen, $CO_2$, helium, neon, argon or mixtures thereof can also be used.

If the Pd precursor compound and Au precursor compound in step (b) are applied from one mixed solution containing the Pd and Au precursor compounds, the solution preferably contains a proportion of Pd precursor compound such that Pd lies in the range of from 0.1 to 15 wt.-%, more preferably in the range of from 0.4 to 11 wt.-% and most preferably in the range of from 0.7 to 7 wt.-%, and a proportion of Au-containing precursor compound such that the proportion of Au lies in the range of from 0.03 to 5 wt.-%, more preferably in the range of from 0.1 to 4 wt.-% and most preferably in the range of from 0.25 to 3 wt.-%, in each case relative to the atomic weight proportion of the metals in solution.

If the Pd precursor compound and the Au precursor compound are applied separately from different solutions, the Pd-containing solution preferably contains Pd in the range of from 0.1 to 20 wt.-%, more preferably in the range of from 0.5 to 15 wt.-% and most preferably in the range of from 1 to 10 wt.-%, and the Au-containing solution preferably contains Au in the range of from 0.1 to 20 wt.-%, more preferably in the range of from 0.5 to 15 wt.-% and most preferably in the range of from 1 to 10 wt.-%, in each case relative to the atomic weight proportion of the metals in solution.

After the step of applying the precursor compounds to the support body in step (b), a drying step preferably takes place before the reducing step. The drying step is preferably carried out at the temperatures mentioned further above, which are also listed for the drying of the applied acetate solution. The drying times as for the drying of the support body to which the acetate solution was applied also apply. The drying preferably takes place either by process gas in the fluid bed or fluidized bed device—if one is being used—by standing in air or in a drying oven, preferably at a temperature in the range of from 60° C. to 120° C. If the drying is carried out in the fluid bed apparatus or the fluidized bed apparatus, it is preferred that the support bodies are present static in the device, i.e. are not swirled by process gas.

In an embodiment of the method according to the invention, the Cu and/or Sn precursor compound is applied to the support body in step (a) simultaneously with the acetate compound. Here it is preferred that the solution containing the acetate compound also contains the Cu and/or Sn precursor compound. The solution that contains the acetate compound as well as the Cu and/or Sn precursor compound contains Cu or Sn, in the form of the Cu or Sn precursor compound respectively, preferably in a quantity in the range of from 0.005 to 1.5 wt.-%, more preferably 0.015 to 0.8 wt.-% and most preferably 0.04 to 0.4 wt.-%, relative to the total weight of the solution containing the acetate compound as well as the Cu and/or Sn precursor compound.

In an alternative embodiment of the method according to the invention, the Cu and/or Sn precursor compound is applied to the support body in step (b) together with the Pd precursor compound and the Au precursor compound. If the Pd precursor compound and the Au precursor compound are applied to the support body sequentially or staggered from two different solutions, either the copper and/or the tin precursor compound is applied at least partially with the application of one of the two Pd and Au precursor compound solutions from a separate solution or the copper and/or the tin precursor compound is applied in one of the two separate Pd precursor compound and Au precursor compound solutions together with the latter.

If the Pd precursor compound and the Au precursor compound are applied simultaneously from two different solutions, the copper and/or tin precursor compound can be placed either in the Pd precursor compound solution or the Au precursor compound solution or in both solutions.

If the Pd precursor compound and the Au precursor compound are applied from one mixed solution, the Cu and/or Sn precursor compound can be applied along with it either simultaneously from a separate solution, or it is present in the mixed solution of the Pd precursor compound and the Au precursor compound. The latter variant is preferred according to the invention.

If the Cu or Sn precursor compound is applied to the support body from a separate solution in step (b), this solution preferably contains copper or tin in the form of the copper or tin precursor compound in a range of from 0.02 to 18 wt.-%, more preferably 0.04 to 11 wt.-% and most preferably 0.1 to 4 wt.-%, relative to the total weight of the solution.

If the Cu and/or Sn precursor compound is applied to the support body in a mixed solution containing the Au, Pd as well as the Cu and/or Sn precursor compound, this mixed solution preferably contains the Cu and/or Sn precursor compound in a quantity in the range of from 0.001 to 3 wt.-%, more preferably 0.005 to 2.2 wt.-% and most preferably 0.015 to 1.4 wt.-%, relative to the total weight of the solution.

In step (b) of the method according to the invention, in addition to the application of the Pd precursor compound, irrespective of whether this is carried out simultaneously with or separately from the application of the Au precursor compound, a pregilding can take place beforehand and/or an aftergilding of the support body afterwards. The step of pregilding or the step of aftergilding is preferably carried out in the same way as in the step of applying the precursor compounds in step (b). Here, the same concentrations and the same precursor compounds as in the production of a solution produced separately in step (b) containing the Au precursor compound are preferably used. In principle, all possible application steps, namely steeping, pore-filling method or spray impregnation, as specified further above for step (b) are again also conceivable here. However, it is particularly preferred that the pregilding or aftergilding takes place by spray impregnation onto support bodies fluidized in a fluid bed or in a fluidized bed, as disclosed further above preferably also for step (b).

If a pregilding is carried out, an optional drying step, such as preferably takes place after step (b) as specified further above, can be carried out after this. Likewise, in the case of the aftergilding after step (b), an identical drying step—as specified for the pregilding—can be carried out.

In the specified pregilding or aftergilding by spray impregnation, preferably the same specifications for the concentration of the Au precursor compound in the solution, the same spraying rate and the same process air apply as in step (b) of the method according to the invention. The embodiment carried out by the pre- or aftergilding is also to be accommodated in this application by the fact that a "sequential" application is spoken of in step (b).

If an aftergilding is carried out, the step of drying the support body is carried out, preferably not immediately after step (b), but preferably only after the step of applying the additional Au precursor compound in the step of aftergilding.

If the pregilding is carried out by spray impregnation in the preferably specified way before step (b), it is preferred that the spraying rate of the spraying-in of the Au precursor compound does not change at the start of the spraying-in of the Pd precursor compound solution. The ratio of the time interval of the simultaneous spraying-in of the two metal precursor compounds in step (b) to the time interval of the spraying-in of the Au precursor compound solution in the step of pre-impregnation preferably lies in the range of from 8 to 1, more preferably in the range of from 6.5 to 1.5 and most preferably in the range of from 5 to 2.

The spraying-on of the solutions containing the precursor compounds is effected in all the method steps of the method according to the invention preferably by atomizing the solution with the help of a spraying nozzle. According to a further preferred embodiment of the method according to the invention, it is provided that the spraying nozzle is designed as an annular gap nozzle and is centrally arranged in the base of the apparatus carrying out the circulating movement of the support bodies. The mouth of the annular gap nozzle in the apparatus is completely circulated by support bodies. It is thereby guaranteed that the free path of the drops of the spray cloud until they meet a shaped body is relatively short and, accordingly, relatively little time remains for the drops to coalesce into larger drops, which could work against the formation of a largely uniform shell thickness.

After the optional step of drying after the step/steps of applying the precursor compounds, a step (c) preferably takes place in which the metal components of the precursor compounds are preferably converted to the elemental metals. This step of reduction is preferably carried out by a temperature treatment in a non-oxidizing atmosphere for the reduction of the metal components of the precursor compounds to the elemental metals. The temperature treatment in a non-oxidizing atmosphere is preferably carried out in a temperature range of from 50 to 400° C., more preferably 50 to 200° C. and most preferably 60 to 150° C. It is particularly preferred that the temperature treatment is carried out in a non-oxidizing atmosphere likewise in a coating device directly after the drying step after the coating with the metal precursor compounds, in particular without the support bodies being removed from the coating device between these steps. This leads to a significant time advantage as well as less abrasion because the time and mechanical strain on the support bodies associated with the decanting of the support bodies cease to apply.

By a non-oxidizing atmosphere is meant in the present invention an atmosphere which contains no, or almost no, oxygen or other gases with an oxidizing action. The non-oxidizing atmosphere can be an atmosphere of inert gas or a reducing atmosphere. A reducing atmosphere can be a gas with a reductive action or a mixture of gas with a reductive action and inert gas.

$N_2$, He, Ne, Ar or mixtures thereof for example are used as inert gas. $N_2$ is particularly preferably used.

The component with a reductive action in the reducing atmosphere is normally to be selected depending on the nature of the reducing metal component, but preferably selected from the group of gases or vaporizable liquids, consisting of ethylene, hydrogen, CO, $NH_3$, formaldehyde, methanol, formic acid and hydrocarbons, or is a mixture of two or more of the above-named gases/liquids. The reducing atmosphere particularly preferably comprises hydrogen as reducing component. It is preferred in particular if the reducing atmosphere is formed from forming gas, a mixture of $N_2$ and $H_2$. The hydrogen content here is in the range of from 1 vol.-% to 15 vol.-%. In the method according to the invention it is reduced for example with hydrogen (2 to 5 vol.-%) in nitrogen as process gas at a temperature in the range of from 60 to 150° C. over a period of for example from 0.25 to 10 hours, preferably 0.5 to 5 hours.

The change named in the second method alternative from inert gas to a reducing atmosphere during the step of reduction preferably takes place by feeding one of the named reducing components to an inert gas atmosphere. Hydrogen gas is preferably fed in here. The feeding of a gas with a reductive action to the inert gas has the advantage that the temperature does not fall substantially, or not down to or below the lower limit of 60° C. desired for the reduction, with the result that there is no need for another cost- and energy-intensive heating due to a corresponding total atmosphere exchange.

The catalyst support obtained after step (c) preferably contains a proportion of Pd in the range of from 0.3 to 2.5 wt.-%, more preferably in the range of from 0.5 to 2.1 wt.-%, even more preferably in the range of from 0.7 to 1.7 wt.-%, relative to the total weight of the catalyst support body after the reduction.

The catalyst support body obtained after step (c) preferably contains a proportion of Au in the range of from 0.1 to 1.2 wt.-%, more preferably 0.2 to 0.9 wt.-% and most preferably 0.3 to 0.6 wt.-%, relative to the total weight of the catalyst support body after the reduction.

The catalyst support body obtained after step (c) preferably contains a proportion of Cu or Sn in the range of from 0.005 to 1 wt.-%, more preferably 0.01 to 0.5 wt.-% and most preferably 0.025 to 0.25 wt.-%, relative to the total weight of the catalyst support body after the reduction.

It is particularly preferred in the method according to the invention that steps (a) and (b) and the optional steps of pre- or aftergilding and the optional steps of drying are carried out in a single device. However, this preferred method can also alternatively be carried out by carrying out step (a) in another device and only the further above-named steps in a single device. Furthermore, it can also be preferred that the step (c) of reduction is carried out in the same device as steps (a) and/or (b). This has the advantage over other methods that the noble metal yield can be greatly optimized, as the abrasion by the introduction and removal of the support bodies into and from different apparatuses between the steps is no longer necessary. Thus, for example with the method according to the invention in which all the steps were carried out in one fluid bed apparatus the loss of noble metal was only 3 wt.-%.

It is particularly preferred that the device in which step (b) and optionally also steps (a) and (c) are carried out is constituted by suitable conventional coating drums, fluidized bed devices or fluid bed devices. Suitable conventional coating drums, fluidized bed devices or fluid bed devices for carrying out the application of the precursor compound in the method according to the invention are known in the state of the art and are marketed for example by companies such as Heinrich Brucks GmbH (Alfeld, Germany), ERWEKA GmbH (Heusenstamm, Germany), Stechel (Germany), DRIAM Anlagenbau GmbH (Eriskirch, Germany), Glatt GmbH (Binzen, Germany), G. S. Divisione Verniciatura (Osteria, Italy), HOFER-Pharma Maschinen GmbH (Weil am Rhein, Germany), L. B. Bohle Maschinen and Verfahren GmbH (Enningerloh, Germany), Lödige Maschinenbau GmbH (Paderborn, Germany), Manesty (Merseyside, Great Britain), Vector Corporation (Marion (IA) USA), Aeromatic-Fielder AG (Bubendorf, Switzerland), GEA Process Engineering (Hampshire, Great Britain), Fluid Air Inc. (Aurora, Ill., USA), Heinen Systems GmbH (Varel, Germany), Hüttlin GmbH (Steinen, Germany), Umang Pharmatech Pvt. Ltd. (Maharashtra, India) and Innojet Technologies (Lörrach, Germany). Particularly preferred fluid bed equipment is sold with the name Innojet® AirCoater or Innojet® Ventilus by Innojet Technologies. Here the IAC-5 coater, the IAC-150 coater or the IAC-025 coater, all from the company Innojet, is particularly preferably used.

A further subject of the present invention is also a shell catalyst which can be obtained using the method according to the invention. The shell catalyst according to the invention differs from conventional shell catalysts for the synthesis of VAM in that it has a significantly higher selectivity and activity in the synthesis of VAM. This is to be attributed to the application of the acetate before the application of the metal precursor compounds and before the reduction, and/or to the fact that the Cu and/or Sn precursor compound is applied along with it in step (a) or step (b). The structural differences clearly present in respect of the better selectivity and activity of the shell catalyst according to the invention compared with conventional catalysts cannot be expressed in physical values at the time of the application. The shell catalyst according to the invention can therefore only be distinguished from conventional catalysts by the manner of its production and the established increased selectivity and activity.

Another embodiment relates to the use of a shell catalyst produced using the method according to the invention for producing alkenyl carboxylic acid esters, in particular VAM and/or allyl acetate monomer. In other words the present invention also relates to a method for producing VAM or allyl acetate in which acetic acid, ethylene or propylene and oxygen or oxygen-containing gases are passed over the catalyst according to the invention. Generally this takes place by passing acetic acid, ethylene and oxygen or oxygen-containing gases over the catalyst according to the invention at temperatures of from 100 to 200° C., preferably 120 to 200° C., and at pressures of from 1 to 25 bar, preferably 1 to 20 bar, wherein non-reacted educts can be recycled. Expediently, the oxygen concentration is kept below 10 vol.-%. Under certain circumstances, however, a dilution with inert gases such as nitrogen or carbon dioxide is also advantageous. Carbon dioxide is particularly suitable for dilution as it is formed in small quantities in the course of VAM synthesis and collects in the recycle gas. The formed vinyl acetate is isolated with the help of suitable methods, which to are described for example in U.S. Pat. No. 5,066,365 A. Equivalent methods have also been published for allyl acetate. Furthermore, it is known that, in such methods for producing vinyl acetate, promoters contained in the catalyst, such as for example Cu or Sn compounds, can also optionally be added in afterwards in order to re-introduce promoter proportions lost during the life of the catalysts in the process. This can take place in the current method for producing alkenyl carboxylic acid esters in that acetate compounds of the promoters are admixed in the acetic acid to be introduced into the process and/or the potassium acetate to be introduced into the process or are added separately.

The invention is described in more detail below using several figures and several embodiment examples without these being understood as limiting.

EXAMPLES

Example 1

Figure 1:
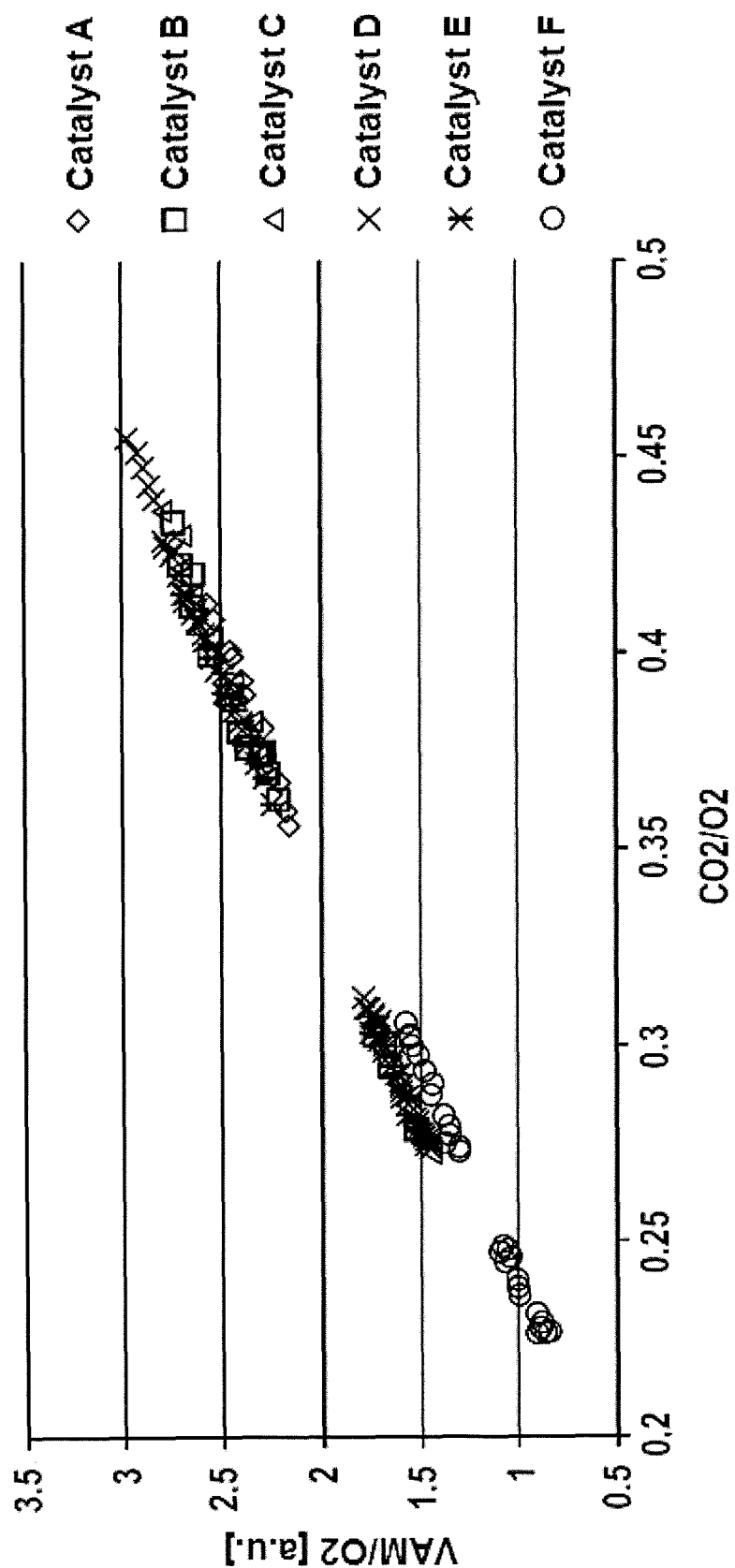
FIG. 1 shows a diagram in which, for the catalysts A to F, the $VAM/O_2$ ratio is plotted against the $CO_2/O_2$ ratio in the synthesis of vinyl acetate monomer.

Production of a Catalyst A 100 g of the support material KA-160 (obtainable from Süd-Chemie AG) is weighed out and impregnated, according to the pore-filling method (incipient wetness), with a mixture of 23.4 g 2 molar KOAc solution, 2.5 g of a $Cu(OAc)_2$ solution (1 wt.-% Cu) and 37 g deionized water. After static drying in a fluidized bed dryer at 90° C. for 35 min, 7.1 g of an aqueous potassium aurate solution (4 wt.-% Au) is diluted with deionized water to 25 g coating solution and this is applied to 100 g support bodies in a first coating step in a coater from Innojet (IAC-025 type) at a spraying rate of 5 g/min. The support bodies are held in a fluid bed. Then, in the second coating step, a mixture of 2.4 g of an aqueous potassium aurate solution (4 wt.-% Au) and 20.2 g of a tetraammine palladium hydroxide solution (4.9 wt.-% Pd) is diluted with deionized water to 35 g coating solution and this is applied to 100 g support bodies at a spraying rate of 5 g/min. The support bodies are held in a fluid bed. After static drying again in a fluidized bed dryer (90° C./35 min), the catalyst is reduced for 30 min at 70° C. with forming gas (5% $H_2$ in $N_2$) statically in a tube furnace.

The elemental analysis of the catalyst, adjusted by the loss on ignition, shows the following proportions:
Pd: 0.93 wt.-%
Au: 0.35 wt.-%
Cu: 0.032 wt.-%

Example 2

Production of a Catalyst B

The catalyst B is produced in the same way as the catalyst A, the only difference being that a mixture of 5 g $Cu(OAc)_2$ solution (1 wt.-% Cu), 34.5 g deionized water and 23.4 g 2 molar KOAc solution is used during the potassium acetate impregnation in the first preparation step.

The elemental analysis of the catalyst shows the following proportions:
Pd: 0.92 wt.-%
Au: 0.35 wt.-%
Cu: 0.091 wt.-%.

Example 3

Production of a Catalyst C

The catalyst C is produced in the same way as the catalyst A, the only difference being that a mixture of 7.5 g $Cu(OAc)_2$ solution (1 wt.-% Cu), 32 g deionized water and 23.4 g 2 molar KOAc solution is used during the potassium acetate impregnation in the first preparation step.

The elemental analysis of the catalyst shows the following proportions:
Pd: 0.91 wt.-%
Au: 0.34 wt.-%
Cu: 0.094 wt.-%.

Example 4

Production of a Catalyst D 100 g of the support material KA-160 (obtainable from Süd-Chemie AG) is weighed out and impregnated, according to the pore-filling method (incipient wetness), with a mixture of 23.4 g 2 molar KOAc solution and 39.5 g deionized water. After static drying in a fluidized bed dryer at 90° C. for 35 min, a mixed solution of 7.1 g of an aqueous potassium aurate solution (4 wt.-% Au) and 5 g of a $Cu(OAc)_2$ solution (1 wt.-% Cu) is diluted with deionized water to 25 g coating solution and this is applied to 100 g support bodies in a first coating step in an IAC-025-type coater from Innojet at a spraying rate of 5 g/min. The support bodies are held in a fluid bed. Then, in a second coating step, a mixture of 2.4 g of an aqueous potassium aurate solution (4 wt.-% Au) and 20.2 g of a tetraammine palladium hydroxide solution (4.9 wt.-% Pd) is diluted with deionized water to 35 g coating solution and this is applied to 100 g support bodies at a spraying rate of 5 g/min (main coating). The support bodies are held in a fluid bed. After static drying again in a fluidized bed dryer (90° C./35 min), the catalyst is reduced for 30 min at 70° C. with forming gas (5% $H_2$ in $N_2$) statically in a tube furnace.

The elemental analysis of the catalyst shows the following proportions:
Pd: 0.89 wt.-%
Au: 0.34 wt.-%
Cu: 0.058 wt.-%.

Example 5

Production of a Catalyst E

The catalyst E is produced like the catalyst D, the difference being that no $Cu(OAc)_2$ is applied in the first coating step. Instead, in the second coating step, a mixture of 5 g of a $Cu(OAc)_2$ solution (1 wt.-% Cu), 2.4 g of an aqueous potassium aurate solution (4 wt.-% Au) and 20.2 g of a tetraammine palladium hydroxide solution (4.9 wt.-% Pd) is diluted with deionized water to 35 g coating solution and this is applied to 100 g support bodies at a spraying rate of 5 g/min.

The elemental analysis of the catalyst shows the following proportions:
Pd: 0.87 wt.-%
Au: 0.35 wt.-%
Cu: 0.055 wt.-%.

Comparison Example 1

Production of a Catalyst F 100 g of the support material KA-160 (obtainable from Süd-Chemie AG) is weighed out and impregnated, according to the pore-filling method (incipient wetness), with a mixture of 23.4 g 2 molar KOAc solution and 39.5 g deionized water. After static drying in a fluidized bed dryer at 90° C. for 35 min, 7.1 g of an aqueous potassium aurate solution (4 wt.-% Au) is diluted with deionized water to 25 g coating solution and this is applied to 100 g support bodies in a first coating step in an IAC-025-type coater from Innojet at a spraying rate of 5 g/min. The support bodies are held in a fluid bed. Then, in a second coating step, a mixture of 2.4 g of an aqueous potassium aurate solution (4 wt.-% Au) and 20.2 g of a tetraammine palladium hydroxide solution (4.9 wt.-% Pd) is diluted with deionized water to 35 g coating solution and applied to 100 g support bodies at a spraying rate of 5 g/min. The support bodies are held in a fluid bed. After static drying again in a fluidized bed dryer (90° C./35 min), the catalyst is reduced for 30 min at 70° C. with forming gas (5% $H_2$ in $N_2$) statically in a tube furnace.

The elemental analysis of the catalyst shows the following proportions:
Pd: 0.9 wt.-%
Au: 0.35 wt.-%

Example 6

Test Results for Catalysts A-F in Respect of their Activity and Selectivity in the Synthesis of Vinyl Acetate Monomer For this, acetic acid, ethylene and oxygen were each passed over the catalysts A to F at a temperature of 138° C./24 hours, 140° C./12 hours, 142° C./12 hours, 144° C./12 hours, 146° C./12 hours, 140° C./12 hours (these are the respective reaction temperatures that apply according to the sequence during the automated execution of the screening protocol, i.e. measurement is carried out for 24 hours at 138° C., then for 12 hours at 140° C., and then for 12 hours at 142° C. reaction temperature, etc.) and a pressure of 8 bar. The concentrations of the components used were: 45% ethylene, 6% $O_2$, 0.9% $CO_2$, 9% methane, 15.5% acetic acid, remainder $N_2$.

Figure 2:
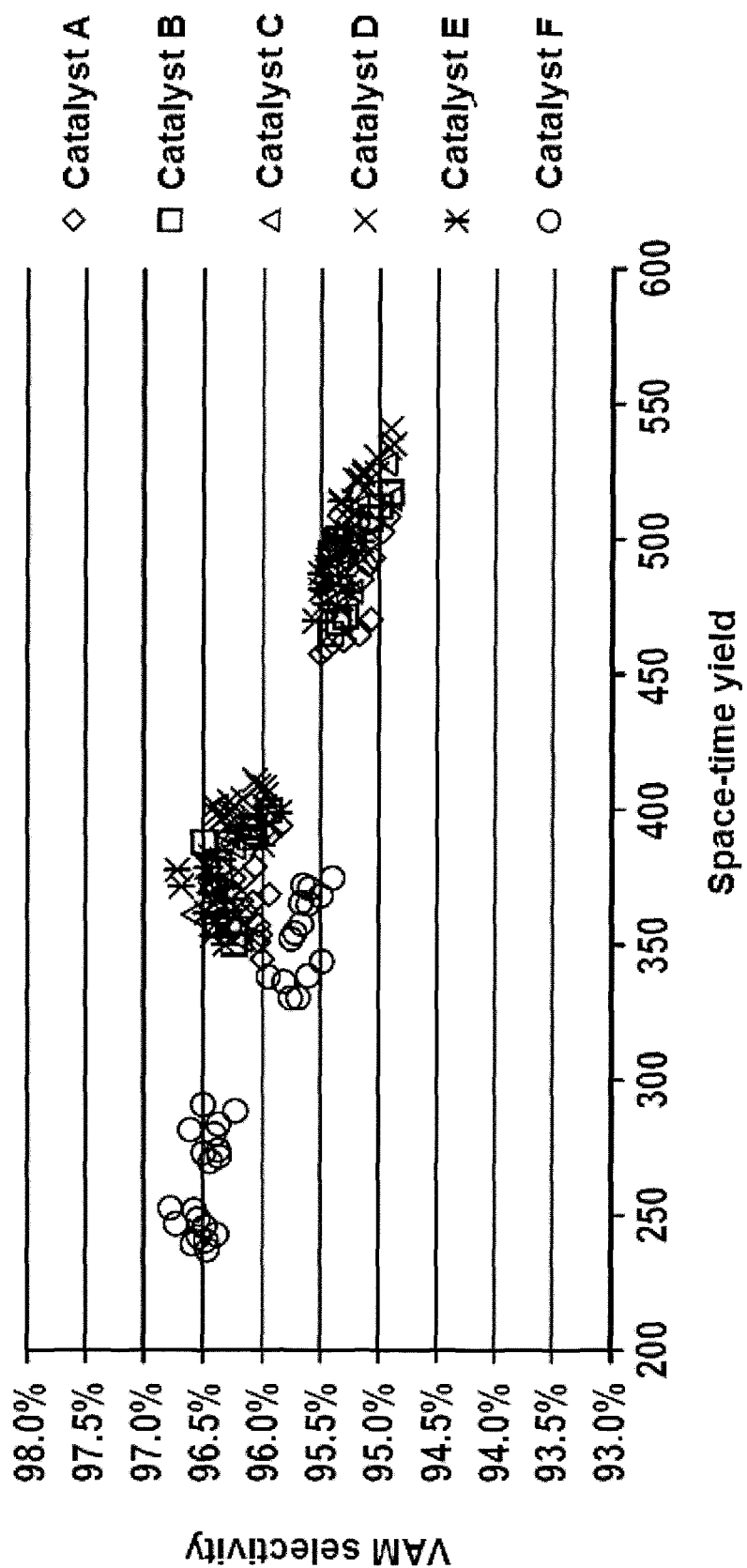
FIG. 2 shows a diagram in which, for the catalysts A to F, the VAM selectivity calculated from VAM and $CO_2$ peaks is plotted against the space-time yield in the synthesis of vinyl acetate monomer.
Figure 3:
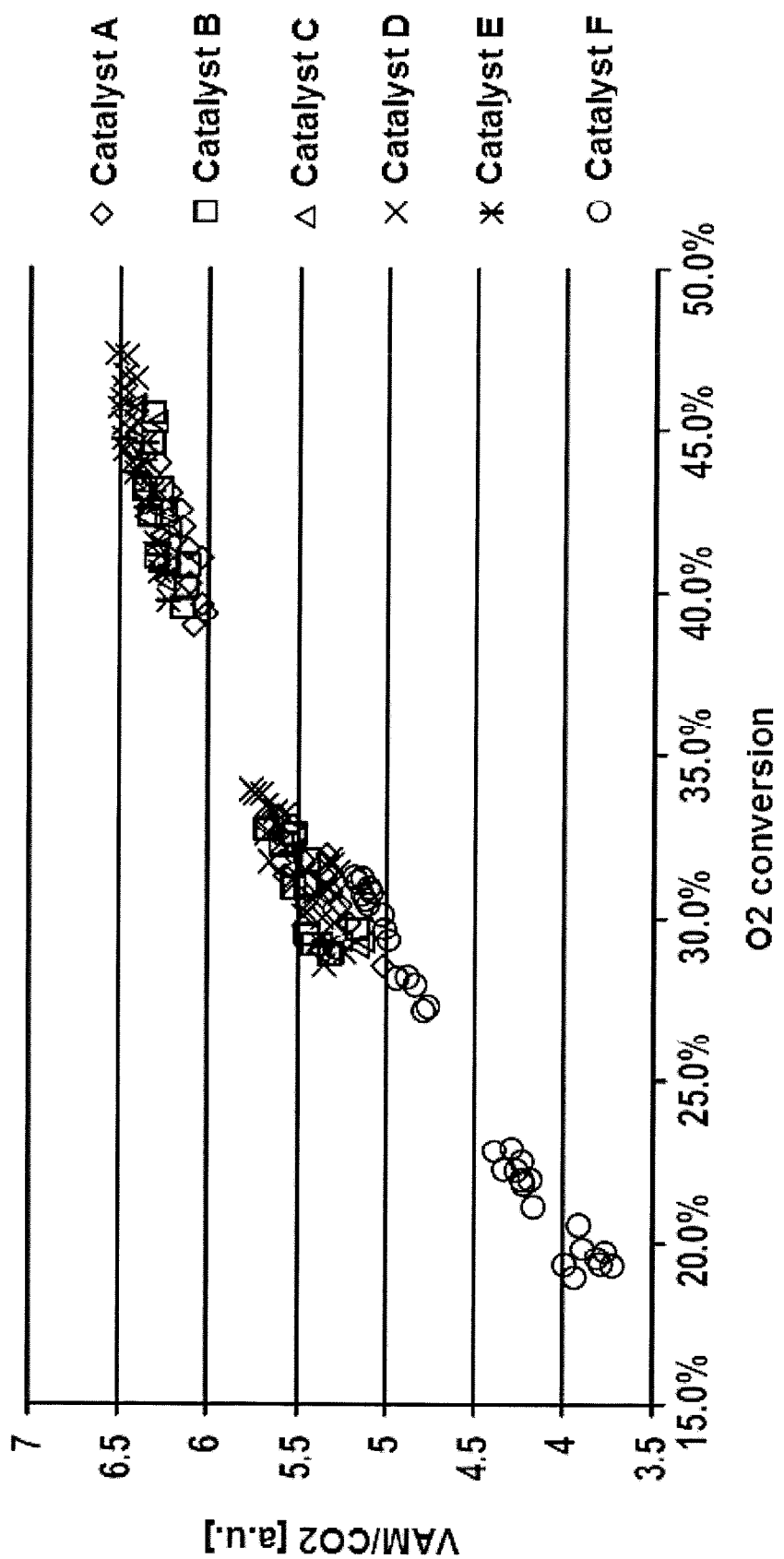
FIG. 3 shows a diagram in which, for the catalysts A to F, the $VAM/CO_2$ ratio is plotted against the $O_2$ conversion in the synthesis of vinyl acetate monomer.
Figure 4:
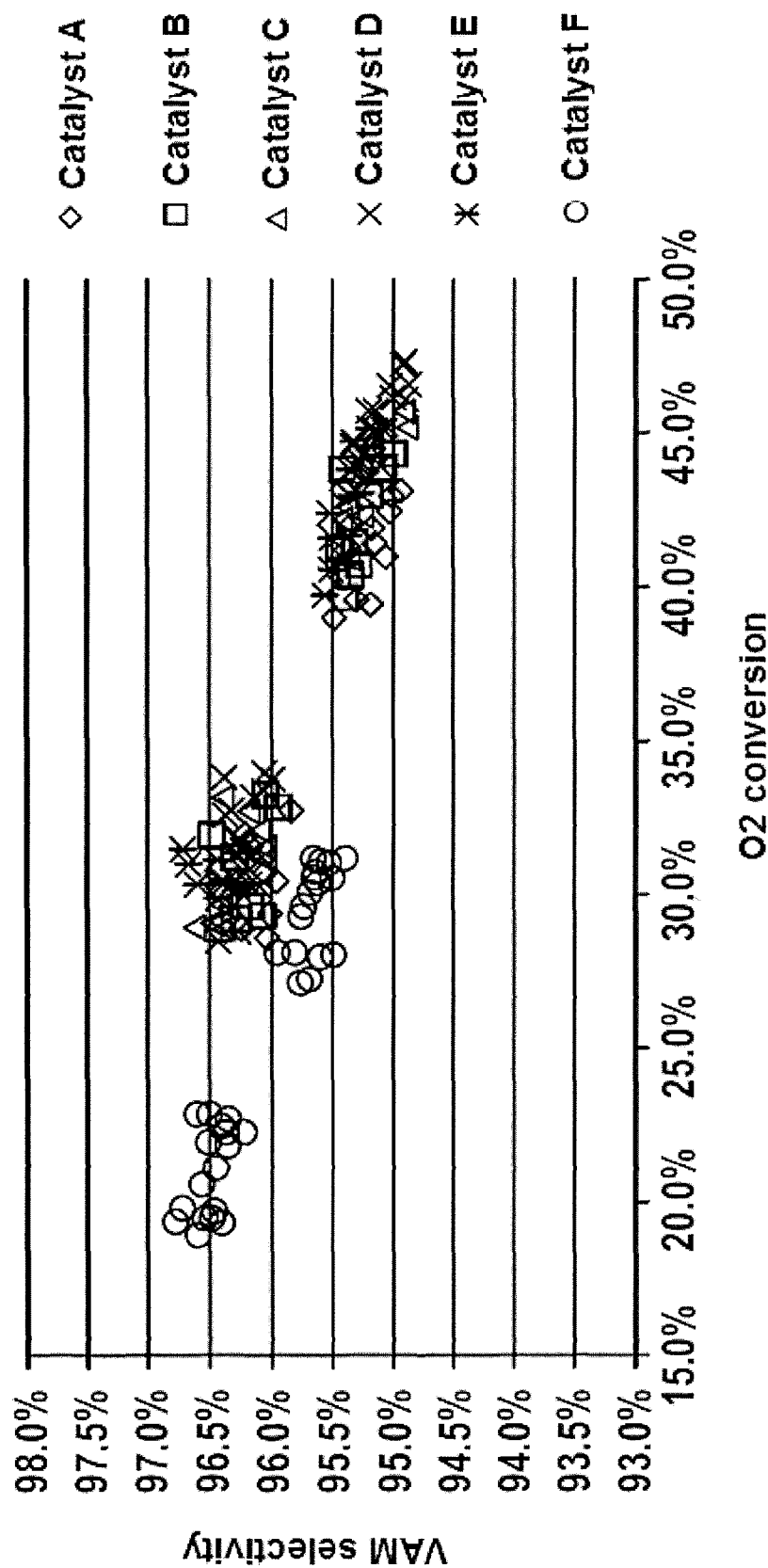
FIG. 4 shows a diagram in which, for the catalysts A to F, the VAM selectivity calculated from VAM and $CO_2$ peaks is plotted against the $O_2$ conversion in the synthesis of vinyl acetate monomer.

Tables 1 to 6 and FIGS. 1 to 4 show the selectivity or the activity of catalysts A to F as a function of the $O_2$ conversion. It can be clearly seen from this that the catalysts A-E produced according to the invention have a much higher activity or selectivity (at the same activity level) than the comparison catalyst F.

TABLE 1

Catalyst A

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.2775 | 1.3921 | 28.6% | 96.0% | 345 | 5.0172 |
| 0.2801 | 1.4258 | 29.2% | 96.1% | 350 | 5.0909 |
| 0.2813 | 1.4336 | 29.4% | 96.0% | 351 | 5.0958 |
| 0.2857 | 1.4623 | 30.6% | 96.1% | 352 | 5.1174 |
| 0.2823 | 1.4558 | 29.4% | 96.0% | 356 | 5.1576 |
| 0.2814 | 1.4425 | 29.3% | 96.0% | 354 | 5.1261 |
| 0.2799 | 1.4625 | 29.4% | 96.2% | 358 | 5.2248 |
| 0.2785 | 1.4717 | 28.9% | 96.2% | 363 | 5.2853 |
| 0.2805 | 1.4740 | 29.3% | 96.2% | 362 | 5.2551 |
| 0.3033 | 1.6758 | 32.7% | 95.9% | 391 | 5.5245 |
| 0.3045 | 1.6838 | 32.6% | 95.9% | 393 | 5.5300 |
| 0.3042 | 1.6828 | 32.9% | 95.9% | 392 | 5.5310 |
| 0.3033 | 1.6893 | 32.7% | 95.9% | 395 | 5.5688 |
| 0.3807 | 2.3009 | 41.0% | 95.1% | 471 | 6.0444 |
| 0.3712 | 2.2707 | 40.3% | 95.3% | 470 | 6.1176 |
| 0.3669 | 2.2108 | 39.5% | 95.2% | 465 | 6.0252 |
| 0.3652 | 2.2069 | 39.6% | 95.3% | 463 | 6.0436 |
| 0.3559 | 2.1621 | 39.0% | 95.5% | 458 | 6.0755 |
| 0.3599 | 2.1854 | 39.4% | 95.4% | 460 | 6.0714 |
| 0.3980 | 2.4793 | 43.1% | 95.3% | 490 | 6.2291 |
| 0.3893 | 2.3999 | 41.5% | 95.2% | 488 | 6.1651 |
| 0.3825 | 2.3352 | 41.2% | 95.3% | 477 | 6.1050 |
| 0.4153 | 2.6113 | 44.0% | 95.0% | 507 | 6.2881 |

TABLE 1-continued

Catalyst A

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.4126 | 2.5817 | 43.2% | 94.9% | 509 | 6.2567 |
| 0.4088 | 2.5484 | 43.1% | 95.0% | 503 | 6.2343 |
| 0.4057 | 2.5411 | 43.3% | 95.1% | 500 | 6.2641 |
| 0.4025 | 2.5071 | 42.8% | 95.1% | 497 | 6.2290 |
| 0.4008 | 2.4720 | 42.5% | 95.1% | 493 | 6.1676 |
| 0.3990 | 2.4586 | 42.5% | 95.1% | 490 | 6.1617 |
| 0.3927 | 2.4136 | 42.0% | 95.2% | 486 | 6.1460 |
| 0.2998 | 1.6664 | 31.9% | 96.2% | 394 | 5.5577 |
| 0.2963 | 1.6181 | 31.0% | 96.1% | 388 | 5.4608 |
| 0.2973 | 1.5841 | 31.9% | 96.2% | 374 | 5.3287 |
| 0.2962 | 1.5866 | 31.2% | 96.1% | 379 | 5.3564 |
| 0.2933 | 1.5278 | 30.4% | 96.0% | 369 | 5.2084 |
| 0.2942 | 1.5749 | 30.9% | 96.1% | 378 | 5.3541 |
| 0.2921 | 1.5729 | 31.1% | 96.3% | 376 | 5.3850 |

TABLE 2

Catalyst B

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.2779 | 1.4291 | 29.2% | 96.2% | 351 | 5.1416 |
| 0.2802 | 1.4505 | 29.6% | 96.2% | 354 | 5.1772 |
| 0.2807 | 1.4588 | 29.6% | 96.2% | 356 | 5.1966 |
| 0.2814 | 1.4590 | 29.9% | 96.2% | 355 | 5.1844 |
| 0.2820 | 1.4757 | 29.7% | 96.2% | 360 | 5.2323 |
| 0.2853 | 1.4936 | 30.8% | 96.2% | 359 | 5.2345 |
| 0.2857 | 1.5134 | 30.9% | 96.3% | 363 | 5.2978 |
| 0.2811 | 1.4539 | 29.4% | 96.1% | 356 | 5.1715 |
| 0.2807 | 1.4898 | 29.3% | 96.2% | 365 | 5.3081 |
| 0.2783 | 1.5031 | 29.2% | 96.4% | 369 | 5.4007 |
| 0.2799 | 1.5172 | 29.5% | 96.4% | 371 | 5.4209 |
| 0.3031 | 1.7162 | 32.8% | 96.0% | 400 | 5.6620 |
| 0.3046 | 1.7159 | 32.9% | 96.0% | 400 | 5.6331 |
| 0.3053 | 1.7261 | 33.2% | 96.0% | 400 | 5.6541 |
| 0.3802 | 2.3821 | 41.2% | 95.3% | 486 | 6.2653 |
| 0.3759 | 2.3481 | 41.2% | 95.4% | 479 | 6.2466 |
| 0.3738 | 2.2912 | 40.7% | 95.3% | 472 | 6.1294 |
| 0.3697 | 2.2704 | 40.4% | 95.4% | 470 | 6.1411 |
| 0.3632 | 2.2233 | 39.6% | 95.4% | 466 | 6.1207 |
| 0.4003 | 2.5361 | 43.4% | 95.3% | 499 | 6.3353 |
| 0.4022 | 2.5530 | 43.0% | 95.2% | 501 | 6.2982 |
| 0.4018 | 2.5387 | 43.9% | 95.4% | 495 | 6.3180 |
| 0.3902 | 2.4432 | 42.1% | 95.3% | 492 | 6.2601 |
| 0.4333 | 2.7407 | 45.5% | 94.9% | 518 | 6.3246 |
| 0.4224 | 2.6908 | 44.8% | 95.1% | 515 | 6.3697 |
| 0.4201 | 2.6583 | 44.3% | 95.0% | 513 | 6.3277 |
| 0.4208 | 2.6726 | 44.6% | 95.1% | 513 | 6.3511 |
| 0.4188 | 2.6542 | 44.5% | 95.1% | 511 | 6.3380 |
| 0.4133 | 2.6123 | 43.9% | 95.1% | 508 | 6.3202 |
| 0.4132 | 2.6255 | 44.0% | 95.2% | 509 | 6.3536 |
| 0.4074 | 2.5819 | 43.6% | 95.2% | 505 | 6.3379 |
| 0.4066 | 2.5733 | 43.7% | 95.2% | 503 | 6.3282 |
| 0.4048 | 2.5570 | 43.3% | 95.2% | 503 | 6.3176 |
| 0.4009 | 2.5175 | 43.1% | 95.3% | 497 | 6.2802 |
| 0.3059 | 1.7195 | 32.9% | 96.2% | 400 | 5.6204 |
| 0.3030 | 1.6785 | 32.5% | 96.2% | 393 | 5.5391 |
| 0.3009 | 1.6703 | 32.3% | 96.2% | 393 | 5.5506 |
| 0.2948 | 1.6432 | 32.0% | 96.5% | 388 | 5.5731 |
| 0.2968 | 1.6332 | 31.6% | 96.3% | 387 | 5.5031 |
| 0.2947 | 1.6230 | 31.0% | 96.2% | 389 | 5.5080 |
| 0.2942 | 1.6133 | 31.7% | 96.4% | 382 | 5.4842 |

TABLE 3

Catalyst C

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.2766 | 1.4342 | 29.1% | 96.3% | 353 | 5.1846 |
| 0.2786 | 1.4365 | 29.3% | 96.2% | 352 | 5.1568 |
| 0.2784 | 1.4530 | 29.7% | 96.4% | 354 | 5.2189 |
| 0.2792 | 1.4516 | 29.5% | 96.3% | 355 | 5.1999 |
| 0.2784 | 1.4659 | 29.6% | 96.4% | 358 | 5.2646 |
| 0.2786 | 1.4645 | 29.6% | 96.3% | 358 | 5.2574 |
| 0.2789 | 1.4729 | 29.5% | 96.3% | 360 | 5.2813 |
| 0.2785 | 1.4724 | 29.2% | 96.3% | 362 | 5.2867 |
| 0.2771 | 1.4811 | 29.3% | 96.4% | 363 | 5.3442 |
| 0.2730 | 1.4656 | 28.9% | 96.6% | 361 | 5.3670 |
| 0.2757 | 1.4722 | 28.9% | 96.4% | 363 | 5.3405 |
| 0.2987 | 1.6660 | 32.2% | 96.1% | 392 | 5.5773 |
| 0.2991 | 1.6666 | 32.4% | 96.1% | 391 | 5.5727 |
| 0.2970 | 1.6668 | 32.0% | 96.1% | 393 | 5.6118 |
| 0.2941 | 1.6331 | 31.3% | 96.1% | 389 | 5.5521 |
| 0.3943 | 2.5000 | 42.3% | 95.2% | 500 | 6.3409 |
| 0.3901 | 2.4560 | 42.6% | 95.3% | 489 | 6.2955 |
| 0.3823 | 2.4166 | 42.2% | 95.5% | 485 | 6.3213 |
| 0.3822 | 2.3718 | 41.6% | 95.3% | 480 | 6.2052 |
| 0.3739 | 2.3275 | 40.9% | 95.4% | 477 | 6.2251 |
| 0.3681 | 2.2965 | 40.3% | 95.5% | 476 | 6.2379 |
| 0.4081 | 2.6006 | 44.1% | 95.3% | 505 | 6.3722 |
| 0.4062 | 2.5923 | 43.7% | 95.3% | 507 | 6.3816 |
| 0.3962 | 2.5109 | 43.2% | 95.4% | 496 | 6.3377 |
| 0.3925 | 2.4532 | 42.5% | 95.3% | 490 | 6.2501 |
| 0.4366 | 2.8055 | 45.7% | 95.0% | 528 | 6.4262 |
| 0.4299 | 2.7109 | 45.2% | 94.9% | 515 | 6.3056 |
| 0.4199 | 2.7037 | 44.6% | 95.2% | 519 | 6.4390 |
| 0.4217 | 2.7019 | 45.1% | 95.2% | 514 | 6.4069 |
| 0.4152 | 2.6673 | 44.5% | 95.3% | 513 | 6.4234 |
| 0.4143 | 2.6547 | 44.3% | 95.2% | 513 | 6.4077 |
| 0.4137 | 2.6532 | 44.3% | 95.2% | 512 | 6.4127 |
| 0.4100 | 2.6190 | 43.8% | 95.2% | 510 | 6.3877 |
| 0.4053 | 2.5652 | 43.6% | 95.3% | 501 | 6.3298 |
| 0.4025 | 2.5622 | 43.4% | 95.3% | 503 | 6.3663 |
| 0.3036 | 1.7328 | 33.2% | 96.4% | 402 | 5.7074 |
| 0.3040 | 1.7183 | 33.0% | 96.3% | 400 | 5.6525 |
| 0.2995 | 1.6756 | 31.9% | 96.2% | 396 | 5.5945 |
| 0.2985 | 1.6681 | 31.6% | 96.2% | 396 | 5.5886 |
| 0.2999 | 1.6607 | 31.9% | 96.2% | 393 | 5.5370 |
| 0.2972 | 1.6507 | 31.8% | 96.3% | 391 | 5.5536 |
| 0.2971 | 1.6299 | 31.7% | 96.2% | 386 | 5.4854 |

TABLE 4

Catalyst D

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.2856 | 1.4951 | 30.3% | 96.1% | 362 | 5.2346 |
| 0.2852 | 1.5037 | 30.3% | 96.2% | 363 | 5.2722 |
| 0.2907 | 1.5376 | 31.4% | 96.1% | 366 | 5.2887 |
| 0.2905 | 1.5473 | 31.7% | 96.2% | 366 | 5.3273 |
| 0.2879 | 1.5371 | 30.8% | 96.2% | 369 | 5.3388 |
| 0.2871 | 1.5206 | 30.7% | 96.2% | 365 | 5.2969 |
| 0.2899 | 1.5656 | 31.4% | 96.2% | 373 | 5.3998 |
| 0.2867 | 1.5446 | 30.5% | 96.2% | 372 | 5.3880 |
| 0.2853 | 1.5425 | 30.4% | 96.3% | 372 | 5.4071 |
| 0.2830 | 1.5467 | 30.0% | 96.3% | 375 | 5.4654 |
| 0.2836 | 1.5467 | 30.2% | 96.3% | 375 | 5.4532 |
| 0.3097 | 1.7765 | 33.8% | 96.0% | 408 | 5.7353 |
| 0.3092 | 1.7649 | 33.8% | 96.0% | 406 | 5.7080 |
| 0.3096 | 1.7808 | 33.9% | 96.0% | 408 | 5.7527 |
| 0.4085 | 2.6043 | 43.9% | 95.1% | 507 | 6.3754 |
| 0.4036 | 2.5713 | 43.7% | 95.2% | 503 | 6.3708 |
| 0.3956 | 2.5161 | 43.1% | 95.3% | 497 | 6.3609 |
| 0.3902 | 2.4615 | 42.4% | 95.3% | 492 | 6.3082 |
| 0.3867 | 2.4321 | 42.1% | 95.3% | 489 | 6.2889 |
| 0.3803 | 2.3973 | 41.8% | 95.4% | 484 | 6.3035 |
| 0.4290 | 2.7696 | 45.8% | 95.2% | 522 | 6.4555 |
| 0.4103 | 2.6312 | 44.1% | 95.3% | 511 | 6.4123 |
| 0.4079 | 2.6083 | 43.9% | 95.3% | 508 | 6.3939 |
| 0.4072 | 2.6058 | 43.9% | 95.3% | 508 | 6.3990 |
| 0.4549 | 2.9644 | 47.3% | 94.9% | 541 | 6.5160 |
| 0.4520 | 2.9190 | 47.3% | 94.9% | 534 | 6.4584 |
| 0.4479 | 2.8899 | 46.6% | 94.9% | 535 | 6.4517 |
| 0.4426 | 2.8590 | 46.1% | 94.9% | 534 | 6.4592 |
| 0.4393 | 2.8423 | 46.2% | 95.0% | 530 | 6.4700 |
| 0.4391 | 2.8376 | 46.1% | 95.0% | 530 | 6.4627 |
| 0.4403 | 2.8304 | 46.5% | 95.0% | 524 | 6.4288 |
| 0.4295 | 2.7843 | 45.6% | 95.1% | 525 | 6.4833 |
| 0.4277 | 2.7727 | 45.7% | 95.2% | 522 | 6.4828 |
| 0.4255 | 2.7496 | 45.1% | 95.1% | 523 | 6.4621 |
| 0.4267 | 2.7327 | 45.2% | 95.1% | 519 | 6.4050 |
| 0.4138 | 2.6744 | 44.6% | 95.3% | 513 | 6.4630 |
| 0.4156 | 2.6677 | 44.4% | 95.2% | 514 | 6.4196 |
| 0.3122 | 1.7773 | 33.4% | 96.0% | 411 | 5.6933 |
| 0.3083 | 1.7385 | 33.2% | 96.1% | 403 | 5.6395 |
| 0.3064 | 1.7455 | 33.8% | 96.4% | 401 | 5.6959 |
| 0.3063 | 1.7118 | 33.2% | 96.2% | 397 | 5.5888 |
| 0.3009 | 1.7039 | 32.6% | 96.4% | 398 | 5.6636 |
| 0.2987 | 1.6833 | 31.7% | 96.3% | 399 | 5.6357 |
| 0.3018 | 1.6995 | 32.7% | 96.3% | 397 | 5.6315 |

TABLE 5

Catalyst E

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.2783 | 1.4351 | 29.6% | 96.3% | 350 | 5.1575 |
| 0.2770 | 1.4452 | 29.5% | 96.4% | 353 | 5.2170 |
| 0.2783 | 1.4598 | 28.9% | 96.2% | 360 | 5.2445 |
| 0.2787 | 1.4704 | 29.9% | 96.4% | 358 | 5.2754 |
| 0.2839 | 1.4657 | 30.4% | 96.2% | 354 | 5.1629 |
| 0.2787 | 1.4642 | 29.6% | 96.3% | 358 | 5.2543 |
| 0.2817 | 1.4984 | 30.3% | 96.4% | 362 | 5.3199 |
| 0.2781 | 1.4657 | 29.6% | 96.4% | 358 | 5.2713 |
| 0.2764 | 1.4696 | 29.1% | 96.4% | 361 | 5.3159 |
| 0.2742 | 1.4677 | 28.6% | 96.4% | 364 | 5.3528 |
| 0.2755 | 1.4740 | 29.0% | 96.4% | 363 | 5.3504 |
| 0.2780 | 1.4874 | 28.8% | 96.3% | 367 | 5.3501 |
| 0.3039 | 1.6995 | 32.4% | 95.9% | 399 | 5.5920 |
| 0.3010 | 1.6973 | 32.6% | 96.1% | 397 | 5.6393 |
| 0.2998 | 1.6709 | 32.6% | 96.1% | 391 | 5.5742 |
| 0.3867 | 2.4297 | 42.1% | 95.3% | 488 | 6.2824 |
| 0.3768 | 2.3742 | 41.5% | 95.5% | 482 | 6.3010 |
| 0.3727 | 2.3285 | 40.7% | 95.4% | 480 | 6.2474 |
| 0.3684 | 2.2929 | 40.6% | 95.5% | 473 | 6.2231 |
| 0.3618 | 2.2473 | 39.8% | 95.5% | 470 | 6.2108 |
| 0.4045 | 2.5837 | 43.8% | 95.3% | 504 | 6.3873 |
| 0.4003 | 2.5223 | 43.2% | 95.3% | 498 | 6.3017 |
| 0.3869 | 2.4374 | 42.4% | 95.5% | 488 | 6.2994 |
| 0.4151 | 2.6856 | 44.7% | 95.3% | 514 | 6.4690 |
| 0.4118 | 2.6176 | 44.1% | 95.2% | 507 | 6.3565 |
| 0.3990 | 2.5242 | 42.9% | 95.3% | 499 | 6.3267 |
| 0.3983 | 2.5176 | 42.9% | 95.3% | 499 | 6.3210 |
| 0.3986 | 2.5263 | 42.7% | 95.3% | 502 | 6.3375 |
| 0.3949 | 2.4943 | 42.5% | 95.3% | 497 | 6.3160 |
| 0.3899 | 2.4655 | 42.1% | 95.4% | 495 | 6.3242 |
| 0.3873 | 2.4389 | 42.1% | 95.5% | 489 | 6.2966 |
| 0.3853 | 2.4164 | 41.7% | 95.4% | 488 | 6.2708 |
| 0.3823 | 2.3941 | 41.5% | 95.5% | 485 | 6.2620 |
| 0.3021 | 1.6376 | 32.0% | 96.0% | 387 | 5.4213 |
| 0.2907 | 1.6012 | 31.1% | 96.4% | 383 | 5.5083 |
| 0.2908 | 1.5888 | 31.4% | 96.5% | 378 | 5.4633 |
| 0.2875 | 1.5884 | 31.5% | 96.7% | 378 | 5.5240 |
| 0.2885 | 1.5687 | 30.6% | 96.4% | 378 | 5.4375 |

TABLE 5-continued

Catalyst E

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.2845 | 1.5509 | 30.4% | 96.6% | 375 | 5.4519 |
| 0.2854 | 1.5580 | 31.0% | 96.7% | 373 | 5.4581 |

TABLE 6

Catalyst F

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.2265 | 0.8550 | 19.4% | 96.6% | 239 | 3.7745 |
| 0.2268 | 0.8476 | 19.3% | 96.5% | 237 | 3.7368 |
| 0.2282 | 0.8663 | 19.3% | 96.4% | 242 | 3.7962 |
| 0.2283 | 0.8646 | 19.6% | 96.5% | 241 | 3.7874 |
| 0.2281 | 0.8767 | 19.5% | 96.5% | 245 | 3.8429 |
| 0.2275 | 0.8677 | 19.5% | 96.5% | 242 | 3.8132 |
| 0.2311 | 0.9025 | 20.5% | 96.6% | 249 | 3.9060 |
| 0.2272 | 0.8843 | 19.8% | 96.7% | 246 | 3.8924 |
| 0.2267 | 0.8949 | 19.0% | 96.6% | 252 | 3.9468 |
| 0.2261 | 0.9024 | 19.3% | 96.8% | 253 | 3.9909 |
| 0.2362 | 0.9859 | 21.1% | 96.4% | 270 | 4.1737 |
| 0.2394 | 1.0045 | 21.9% | 96.4% | 272 | 4.1957 |
| 0.2394 | 1.0103 | 21.9% | 96.4% | 274 | 4.2192 |
| 0.2384 | 1.0085 | 21.9% | 96.5% | 273 | 4.2305 |
| 0.2819 | 1.3801 | 28.1% | 95.5% | 345 | 4.8961 |
| 0.2789 | 1.3511 | 27.9% | 95.6% | 338 | 4.8441 |
| 0.2752 | 1.3572 | 28.2% | 95.9% | 338 | 4.9316 |
| 0.2767 | 1.3503 | 28.1% | 95.8% | 337 | 4.8800 |
| 0.2739 | 1.3097 | 27.2% | 95.7% | 331 | 4.7813 |
| 0.2727 | 1.3068 | 27.2% | 95.8% | 330 | 4.7919 |
| 0.2932 | 1.4757 | 30.1% | 95.7% | 358 | 5.0326 |
| 0.2897 | 1.4495 | 29.7% | 95.7% | 354 | 5.0042 |
| 0.2872 | 1.4335 | 29.3% | 95.8% | 352 | 4.9907 |
| 0.3052 | 1.5724 | 31.2% | 95.4% | 375 | 5.1526 |
| 0.3020 | 1.5494 | 31.1% | 95.5% | 370 | 5.1304 |
| 0.3011 | 1.5592 | 31.2% | 95.6% | 372 | 5.1774 |
| 0.3012 | 1.5535 | 31.1% | 95.6% | 371 | 5.1575 |
| 0.2993 | 1.5247 | 30.8% | 95.6% | 366 | 5.0946 |
| 0.2981 | 1.5290 | 30.7% | 95.6% | 367 | 5.1290 |
| 0.2998 | 1.5309 | 30.6% | 95.5% | 368 | 5.1060 |
| 0.2971 | 1.5192 | 30.6% | 95.6% | 366 | 5.114 |
| 0.2970 | 1.5149 | 30.4% | 95.6% | 365 | 5.1005 |
| 0.2473 | 1.0859 | 22.8% | 96.5% | 291 | 4.3914 |
| 0.2480 | 1.0701 | 22.3% | 96.2% | 289 | 4.3154 |
| 0.2469 | 1.0526 | 22.7% | 96.4% | 282 | 4.2631 |
| 0.2455 | 1.0467 | 22.2% | 96.4% | 283 | 4.2639 |
| 0.2449 | 1.0508 | 22.9% | 96.6% | 281 | 4.2903 |
| 0.2454 | 1.0380 | 22.5% | 96.4% | 279 | 4.2293 |

Example 7

Production of a Catalyst G 100 g of the support material KA-160 (obtainable from Süd-Chemie AG) is weighed out and impregnated, according to the pore-filling method (incipient wetness), with a mixture of 23.4 g 2 molar KOAc solution, 25 g of a $Cu(OAc)_2$ solution (2 wt.-% Cu) and 12.5 g deionized water. After static drying in a fluidized bed dryer at 90° C. for 35 min, 13.2 g of an aqueous potassium aurate solution (4 wt.-% Au) is diluted with deionized water to 25 g coating solution and this is applied to 100 g support bodies in a first coating step in a coater from Innojet (IAC-025 type) at a spraying rate of 5 g/min. The support bodies are held in a fluid bed. Then, in a second coating step, a mixture of 4.4 g of an aqueous potassium aurate solution (4 wt.-% Au) and 30.6 g of a tetraammine palladium hydroxide solution (3.8 wt.-% Pd) is applied to 100 g support bodies at a spraying rate of 5 g/min. The support bodies are held in a fluid bed. After static drying again in a fluidized bed dryer (90° C./35 min), the catalyst is reduced for 30 min at 70° C. with forming gas (5% $H_2$ in $N_2$) statically in a tube furnace.

The elemental analysis of the catalyst, adjusted by the loss on ignition, shows the following proportions:
Pd: 1.08 wt.-%
Au: 0.65 wt.-%
Cu: 0.48 wt.-%.

Example 8

Production of a Catalyst H

The catalyst H is produced in the same way as the catalyst A, the only difference being that 25 g of a $Cu(OAc)_2$ solution with a Cu concentration of 1 wt.-% is used during the potassium acetate impregnation in the first step.

The elemental analysis of the catalyst shows the following proportions:
Pd: 0.91 wt.-%
Au: 0.36 wt.-%
Cu: 0.23 wt.-%.

Example 9

Production of a Catalyst I

The catalyst I is produced in the same way as the catalyst D, the only difference being that, instead of 5 g of a $Cu(OAc)_2$ solution (1 wt.-% Cu), 0.15 g $K_2SnO_3$ is mixed with the potassium aurate solution in the first coating step.

The elemental analysis of the catalyst shows the following proportions:
Pd: 0.88 wt.-%
Au: 0.35 wt.-%
Sn: 0.056 wt.-%.

Example 10

Production of a Catalyst J

The catalyst J is produced in the same way as the catalyst B, the only difference being that in the first step, instead of 5 g of a $Cu(OAc)_2$ solution (1 wt.-% Cu), 0.15 g $K_2SnO_3$ is mixed with the potassium acetate impregnating solution.

The elemental analysis of the catalyst shows the following proportions:
Pd: 0.90 wt.-%
Au: 0.35 wt.-%
Sn: 0.045 wt.-%.

Comparison Example 2

Production of a Catalyst K 100 g of the support material KA-160 (obtainable from aid-Chemie AG) is weighed out and impregnated, according to the pore-filling method (incipient wetness), with a solution of 0.97 g copper chloride dihydrate in 63.0 g deionized water. The Cu was fixed on the support for 2.5 h in an NaOH solution (1.1 g NaOH in 220 g deionized water) and the supernatant solution was decanted off. The support was then washed Cl-free with deionized water and dried in the nitrogen stream at 150° C. The Pd was applied via the pore-filling method (incipient wetness) by impregnating the support loaded with Cu(OH)$_2$ with a mixture of 10.9 g Na$_2$PdCl$_4$ solution (12.36 wt.-% Pd) and 52.2 g deionized water. Then, the Pd was likewise fixed on the support in an NaOH solution (2.5 g NaOH in 220 g deionized water) and the Pd- and Cu-containing support was again washed Cl-free with deionized water. The interim catalyst is dried at 90° C. for 35 min in a fluidized bed dryer and reduced at 70° C. for 30 min in a tube furnace statically with forming gas (5% H$_2$ in N$_2$). The gold is then likewise applied via the pore-filling method (incipient wetness). The interim catalyst is impregnated with a mixture of 18.3 g potassium aurate solution (4 wt.-% Au) and 44.6 g deionized water. The catalyst is then reduced with forming gas (5% H$_2$ in N$_2$) at 100° C. for 30 min statically in a tube furnace. Then, the catalyst is again impregnated, via the pore-filling method (incipient wetness), with a potassium acetate solution (7.6 g potassium acetate dissolved in 55.4 g deionized water). Drying then took place at 100° C. in a fluidized bed dryer.

The elemental analysis of the catalyst shows the following proportions:
Pd: 1.31 wt.-%
Au: 0.82 wt.-%
Cu: 0.32 wt.-%.

Example 11

Test Results for Catalysts G-K in Respect of their Activity and Selectivity in the Synthesis of Vinyl Acetate Monomer For this, acetic acid, ethylene and oxygen were each passed over the catalysts G to K at a temperature of 138° C./24 hours, 140° C./12 hours and 142° C./12 hours (these are the respective reaction temperatures that apply according to the sequence during the automated execution of the screening protocol, i.e. measurement is carried out for 24 hours at 138° C., then for 12 hours at 140° C., and then for 12 hours at 142° C. reaction temperature) and a pressure of 5 bar. The concentrations of the components used were: 38% ethylene, 5% O$_2$, 0.9% CO$_2$, 9% methane, 12% acetic acid, remainder N$_2$.

Figure 5:
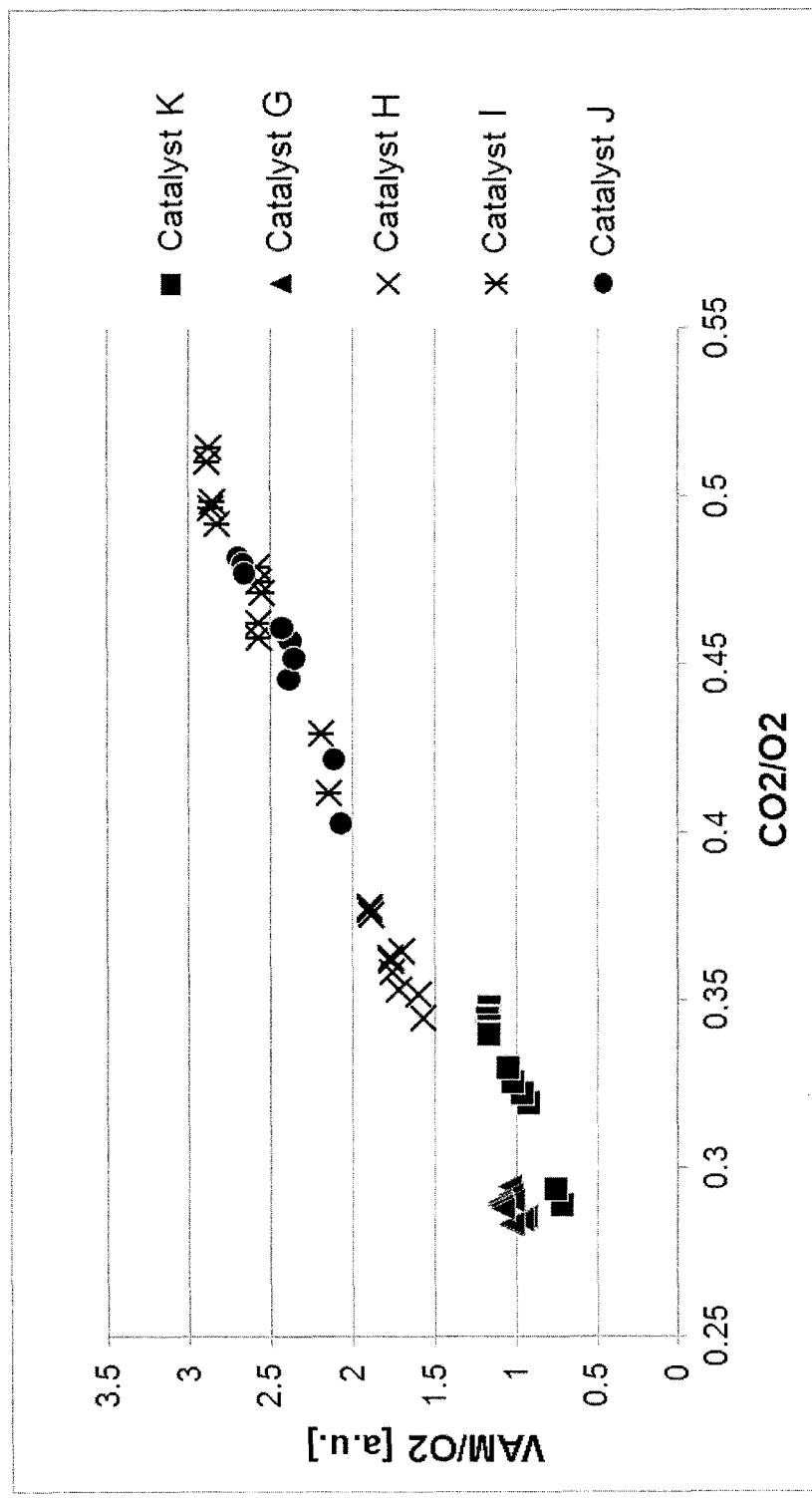
FIG. 5 shows a diagram in which, for the catalysts G to K, the $VAM/O_2$ ratio is plotted against the $CO_2/O_2$ ratio in the synthesis of vinyl acetate monomer.
Figure 6:
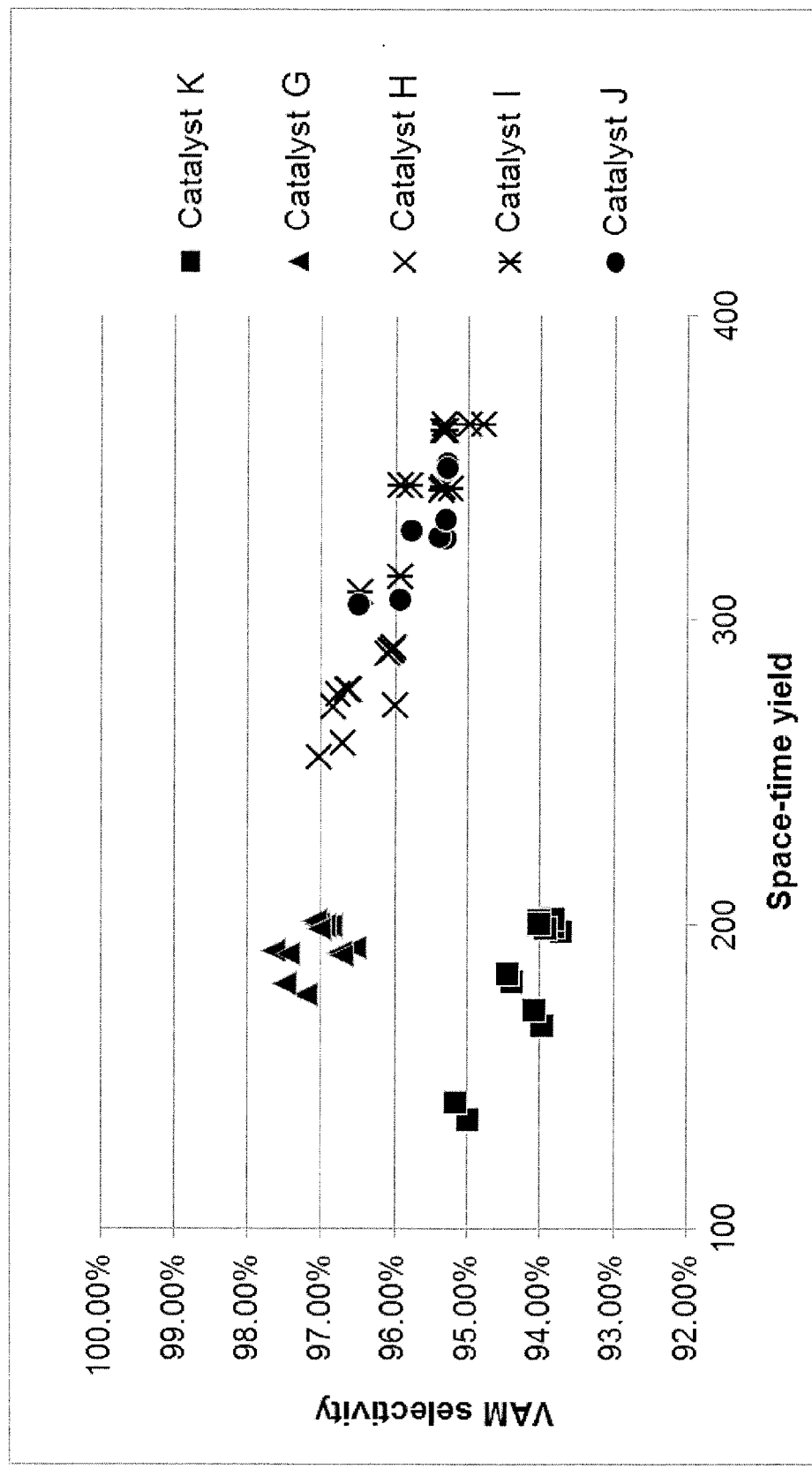
FIG. 6 shows a diagram in which, for the catalysts G to K, the VAM selectivity calculated from VAM and $CO_2$ peaks is plotted against the space-time yield in the synthesis of vinyl acetate monomer.
Figure 7:
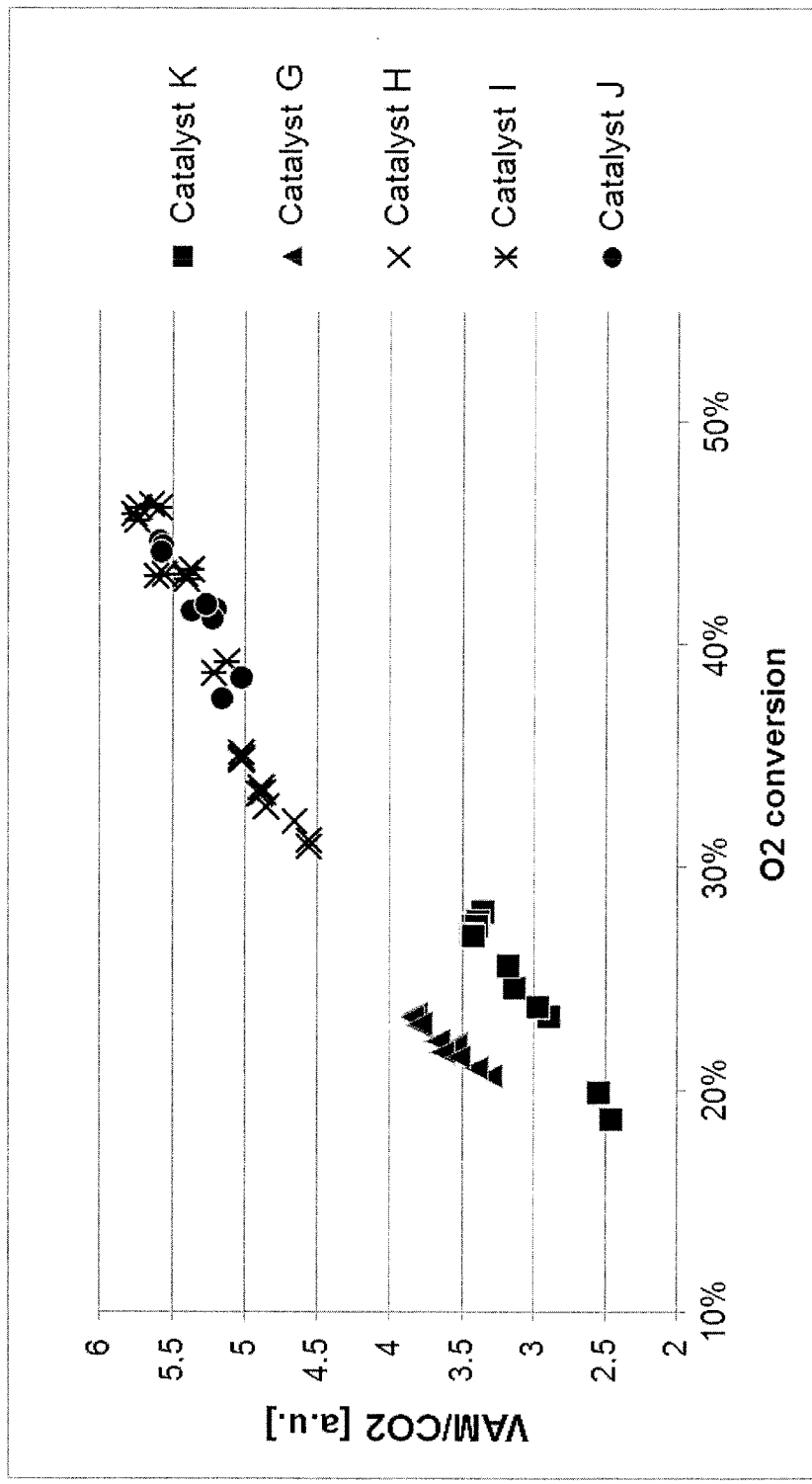
FIG. 7 shows a diagram in which, for the catalysts G to K, the $VAM/CO_2$ ratio is plotted against the $O_2$ conversion in the synthesis of vinyl acetate monomer.
Figure 8:
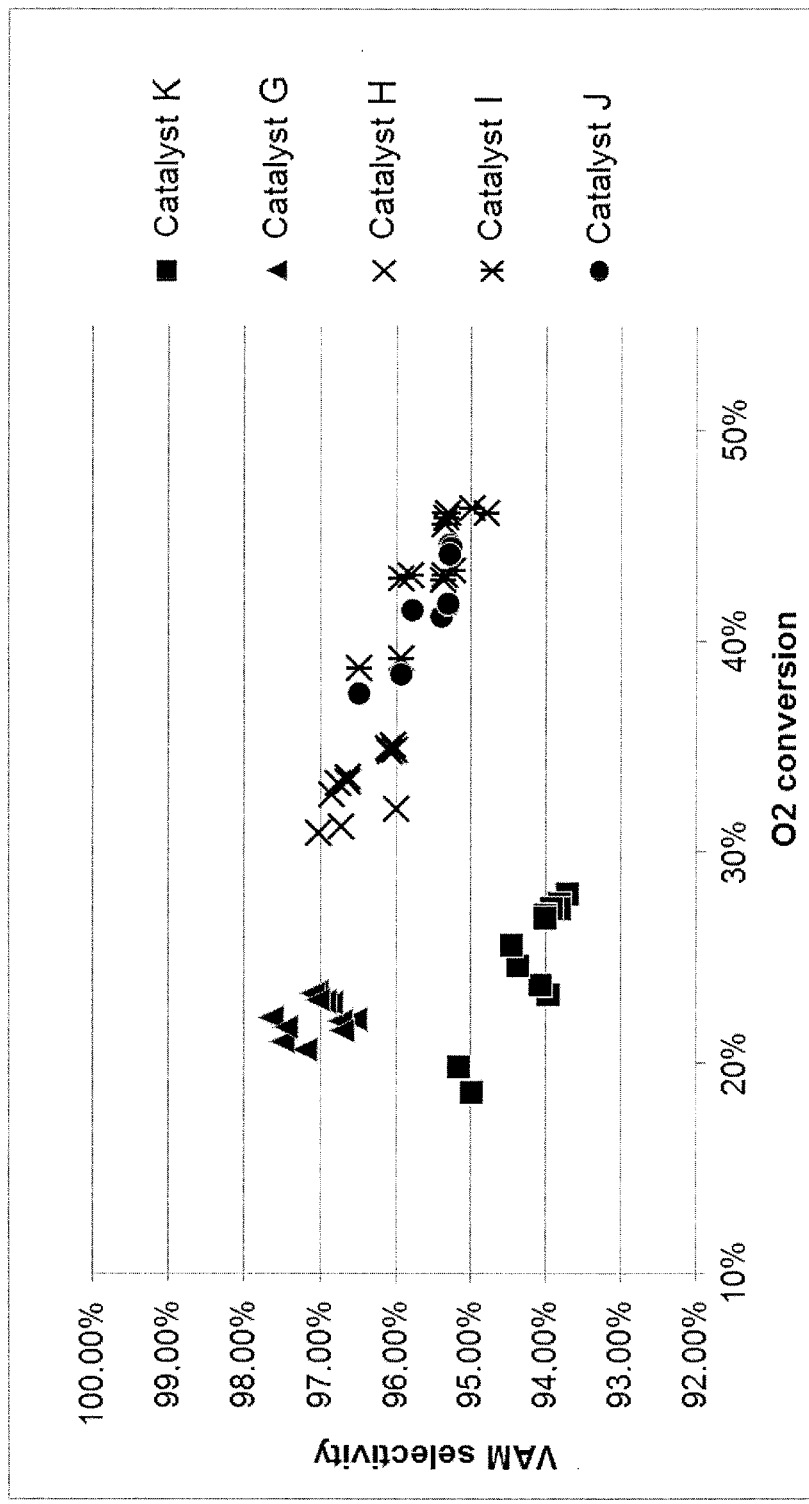
FIG. 8 shows a diagram in which, for the catalysts G to K, the VAM selectivity calculated from VAM and $CO_2$ peaks is plotted against the $O_2$ conversion in the synthesis of vinyl acetate monomer.

Tables 7 to 11 and FIGS. 5 to 8 show the selectivity or the activity of catalysts G to K as a function of the O$_2$ conversion. It can be clearly seen from this that the catalysts G-J produced according to the invention have a much higher activity or selectivity (at the same activity level) than the comparison catalyst K.

TABLE 7

Catalyst G

| CO$_2$/O$_2$ [a.u.] | VAM/O$_2$ [a.u.] | O$_2$ conversion | VAM selectivity | Space-time yield [g VAM/l*h] | VAM/CO$_2$ [a.u.] |
|---|---|---|---|---|---|
| 0.2853 | 0.9451 | 20.6% | 97.2% | 177 | 3.3125 |
| 0.2844 | 0.9676 | 21.0% | 97.5% | 180 | 3.4024 |
| 0.2945 | 1.0461 | 22.0% | 96.6% | 192 | 3.5517 |
| 0.2921 | 1.0379 | 22.0% | 96.7% | 191 | 3.5537 |
| 0.2832 | 1.0412 | 22.1% | 97.6% | 191 | 3.6769 |
| 0.2834 | 1.0310 | 21.7% | 97.5% | 190 | 3.6380 |
| 0.2902 | 1.0240 | 21.5% | 96.7% | 190 | 3.5286 |
| 0.2895 | 1.1070 | 23.4% | 97.1% | 200 | 3.8236 |
| 0.2888 | 1.1102 | 23.3% | 97.1% | 201 | 3.8437 |
| 0.2894 | 1.0972 | 22.8% | 96.9% | 200 | 3.7912 |
| 0.2887 | 1.0969 | 22.9% | 97.0% | 199 | 3.8001 |
| 0.2879 | 1.0927 | 23.0% | 97.0% | 198 | 3.7952 |

TABLE 8

Catalyst H

| CO$_2$/O$_2$ [a.u.] | VAM/O$_2$ [a.u.] | O$_2$ conversion | VAM selectivity | Space-time yield [g VAM/l*h] | VAM/CO$_2$ [a.u.] |
|---|---|---|---|---|---|
| 0.3447 | 1.5694 | 31.0% | 97.0% | 255 | 4.5524 |
| 0.3520 | 1.6043 | 31.2% | 96.7% | 260 | 4.5571 |
| 0.3629 | 1.7719 | 33.6% | 96.6% | 277 | 4.8828 |
| 0.3619 | 1.7657 | 33.4% | 96.6% | 277 | 4.8793 |
| 0.3586 | 1.7546 | 33.3% | 96.8% | 276 | 4.8934 |
| 0.3649 | 1.6988 | 32.1% | 96.0% | 272 | 4.6557 |
| 0.3535 | 1.7143 | 32.7% | 96.8% | 272 | 4.8494 |
| 0.3774 | 1.8965 | 34.9% | 96.0% | 291 | 5.0250 |
| 0.3783 | 1.8981 | 35.2% | 96.0% | 290 | 5.0175 |
| 0.3756 | 1.8852 | 34.9% | 96.1% | 289 | 5.0188 |
| 0.3758 | 1.8873 | 34.8% | 96.1% | 290 | 5.0227 |

TABLE 9

Catalyst I

| CO$_2$/O$_2$ [a.u.] | VAM/O$_2$ [a.u.] | O$_2$ conversion | VAM selectivity | Space-time yield [g VAM/l*h] | VAM/CO$_2$ [a.u.] |
|---|---|---|---|---|---|
| 0.4119 | 2.1437 | 38.7% | 96.5% | 309 | 5.2041 |
| 0.4293 | 2.1964 | 39.2% | 95.9% | 315 | 5.1157 |
| 0.4790 | 2.5713 | 43.4% | 95.2% | 343 | 5.3675 |
| 0.4624 | 2.5684 | 43.2% | 95.8% | 344 | 5.5545 |
| 0.4746 | 2.5659 | 43.2% | 95.4% | 344 | 5.4070 |
| 0.4582 | 2.5667 | 43.0% | 95.9% | 345 | 5.6013 |
| 0.4713 | 2.5454 | 42.9% | 95.4% | 343 | 5.4007 |
| 0.5104 | 2.8781 | 46.3% | 95.0% | 364 | 5.6393 |
| 0.5146 | 2.8706 | 46.1% | 94.8% | 365 | 5.5786 |
| 0.4965 | 2.8575 | 45.9% | 95.3% | 365 | 5.7551 |
| 0.4984 | 2.8538 | 46.1% | 95.3% | 363 | 5.7262 |
| 0.4920 | 2.8228 | 45.6% | 95.3% | 362 | 5.7368 |

TABLE 10

Catalyst J

| CO$_2$/O$_2$ [a.u.] | VAM/O$_2$ [a.u.] | O$_2$ conversion | VAM selectivity | Space-time yield [g VAM/l*h] | VAM/CO$_2$ [a.u.] |
|---|---|---|---|---|---|
| 0.4029 | 2.0744 | 37.6% | 96.5% | 305 | 5.1482 |
| 0.4218 | 2.1177 | 38.5% | 95.9% | 307 | 5.0210 |
| 0.4573 | 2.3753 | 41.6% | 95.3% | 327 | 5.1946 |
| 0.4457 | 2.3891 | 41.5% | 95.8% | 329 | 5.3603 |
| 0.4521 | 2.3587 | 41.2% | 95.4% | 327 | 5.2177 |
| 0.4608 | 2.4267 | 41.8% | 95.3% | 333 | 5.2660 |
| 0.4821 | 2.6929 | 44.6% | 95.3% | 352 | 5.5860 |
| 0.4799 | 2.6691 | 44.5% | 95.3% | 350 | 5.5615 |
| 0.4772 | 2.6573 | 44.2% | 95.3% | 350 | 5.5684 |

TABLE 11

Catalyst K

| CO$_2$/O$_2$ [a.u.] | VAM/O$_2$ [a.u.] | O$_2$ conversion | VAM selectivity | Space-time yield [g VAM/l*h] | VAM/CO$_2$ [a.u.] |
|---|---|---|---|---|---|
| 0.289 | 0.709 | 18.7% | 95.0% | 136 | 2.452 |
| 0.294 | 0.749 | 19.9% | 95.1% | 141 | 2.550 |
| 0.320 | 0.923 | 23.3% | 94.0% | 167 | 2.887 |
| 0.322 | 0.958 | 23.8% | 94.1% | 172 | 2.970 |
| 0.326 | 1.019 | 24.6% | 94.4% | 181 | 3.129 |
| 0.330 | 1.048 | 25.6% | 94.4% | 184 | 3.174 |
| 0.348 | 1.167 | 28.0% | 93.7% | 198 | 3.352 |
| 0.345 | 1.168 | 27.6% | 93.8% | 199 | 3.382 |

TABLE 11-continued

Catalyst K

| $CO_2/O_2$ [a.u.] | $VAM/O_2$ [a.u.] | $O_2$ conversion | VAM selectivity | Space-time yield [g VAM/l*h] | $VAM/CO_2$ [a.u.] |
|---|---|---|---|---|---|
| 0.345 | 1.180 | 27.4% | 93.8% | 202 | 3.418 |
| 0.343 | 1.162 | 27.4% | 93.9% | 199 | 3.393 |
| 0.341 | 1.170 | 27.0% | 94.0% | 201 | 3.433 |
| 0.340 | 1.163 | 26.9% | 94.0% | 200 | 3.419 |

What is claimed:

1. A method for producing a shell catalyst, in which the following steps are carried out:
 (a) applying a water-soluble acetate compound comprising acetate anions to a support body; and
 (b) sequentially or simultaneously applying a Pd precursor compound and an Au precursor compound to the support body obtained after step (a);
wherein in one of steps (a) and (b) a Cu and/or Sn precursor compound is additionally applied to the support body.

2. The method according to claim 1, wherein the acetate compound is an alkali or acetate.

3. The method according to claim 1, wherein the Pd and/or Au and/or Cu and/or Sn precursor compound is a chlorine- or chloride-free precursor compound.

4. The method according to claim 1, wherein the application in step (a) is carried out by wet-chemical impregnation.

5. The method according to claim 4, wherein the wet-chemical impregnation is carried out by the pore-filling method.

6. The method according to one of claim 1, wherein the application to the support body in step (b) is carried out by spray impregnation of one solution or several solutions containing the precursor compounds.

7. The method according to claim 6, wherein the support bodies are swirled by a process gas during the spray impregnation.

8. The method according to claim 7, wherein swirling of the support bodies is effected in a fluid bed or a fluidized bed.

9. The method according to claim 1, wherein a step (c) of reducing the metal components of the precursor compounds is carried out after step (b).

10. The method according to claim 9, wherein steps (b) and (c) are carried out in one device which is the same device for steps (b) and (c).

11. The method according to claim 10, wherein the support bodies are present static during step (c).

12. The method according to claim 1, wherein a step (b1) of drying the support bodies is carried out after step (b).

13. The method according to claim 12, wherein steps (b), (b1) and (c) are carried out in one device which is the same device for steps (b), (b1) and (c).

14. A shell catalyst obtained using a method according to claim 1.

15. A method for producing alkenyl carboxylic acid esters comprising catalyzing the reaction of a mixture of ethylene, oxygen, and acetic acid with the shell catalyst of claim 14 to form an alkenyl carboxylic acid ester.

* * * * *